United States Patent
Rhee et al.

(10) Patent No.: US 10,563,210 B2
(45) Date of Patent: *Feb. 18, 2020

(54) METHOD FOR PRODUCING INTERLEUKIN-2 PROTEIN USING METHYLOTROPHIC YEAST

(71) Applicant: SOONCHUNHYANG UNIVERSITY INDUSTRY ACADEMY COOPERATION FOUNDATION, Chungcheongnam-do (KR)

(72) Inventors: Sang-Ki Rhee, Seoul (KR); Eun O Park, Chungcheongnam-do (KR); Hoon Seo, Seoul (KR); Guang Jin Choi, Gyeonggi-do (KR); Keon-Hyoung Song, Chungcheongnam-do (KR)

(73) Assignee: SOONCHUNHYANG UNIVERSITY INDUSTRY ACADEMY COOPERATION FOUNDATION, Chungcheongnam-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/523,290

(22) PCT Filed: May 13, 2015

(86) PCT No.: PCT/KR2015/004788
§ 371 (c)(1),
(2) Date: Oct. 10, 2017

(87) PCT Pub. No.: WO2016/068428
PCT Pub. Date: May 6, 2016

(65) Prior Publication Data
US 2018/0237488 A1    Aug. 23, 2018

(30) Foreign Application Priority Data
Oct. 30, 2014   (KR) .................. 10-2014-0149034
Oct. 30, 2014   (KR) .................. 10-2014-0149042

(51) Int. Cl.
*C12N 15/85*   (2006.01)
*C12N 15/81*   (2006.01)
*C12P 21/02*   (2006.01)
*C07K 14/55*   (2006.01)
*C07K 14/765*  (2006.01)

(52) U.S. Cl.
CPC .............. *C12N 15/81* (2013.01); *C07K 14/55* (2013.01); *C07K 14/765* (2013.01); *C12P 21/02* (2013.01); *C07K 2319/31* (2013.01); *C07K 2319/50* (2013.01)

(58) Field of Classification Search
CPC ........ C12N 15/85; C07K 14/55; C07K 14/765
See application file for complete search history.

(56) References Cited

FOREIGN PATENT DOCUMENTS

| KR | 10-2006-0050412 | 5/2006 |
| KR | 10-2006-0131445 | 12/2006 |
| KR | 10-2011-0104348 | 9/2011 |

OTHER PUBLICATIONS

Lei et al. Protein Expression and Purification 84:154-160, 2012 (Year: 2012).*
Kang, H.A. et al., "Development of Expression Systems for the Production of Recombinant Human Serum Albumin Using the MOX Promoter in Hansenula polymorpha DL-1," Biotech. Bioengin. 7:175-185, John Wiley & Sons, Hoboken, NJ (2001).
Melder, R.J. et al., "Pharmacokinetics and In Vitro and In Vivo Anti-Tumor Response of an Interleukin-2-Human Serum Albumin Fusion Protein in Mice," Cancer Immunol. Immunother. 54:535-547, Springer-Verlag GmbH, Berlin, Germany (2005).
Song, H., et al., "Pichia Augusta Hypothetical Protein Gene, Complete CDs; and MOX Gene, Promoter Region," GenBank Assession No. AY550079.1 (2004).
Yu, Z., et al., "Homo sapiens Serum Albumin Precursor, mRNA, Complete CDs," GenBank Assession No. AY728024.1 (2004).
English Translation of and International Search Report of PCT/KR2015/004787, WIPO (dated Jul. 8, 2015).
English Translation of and International Search Report of PCT/KR2015/004788, WIPO (dated Aug. 18, 2015).

* cited by examiner

*Primary Examiner* — Marcia S Noble
(74) *Attorney, Agent, or Firm* — Potomac Law Group, PLLC

(57) ABSTRACT

The present invention relates to a method for producing an interleukin-2 protein using methylotrophic yeast. The method for producing interleukin-2 according to the present invention shows high cell growth and protein synthesis rates by use of the established optimal cell line, and produces a large amount of a protein comprising interleukin-2 by use of the established optimal culture conditions utilizing methanol that is an inexpensive carbon source. In addition, the method according to the present invention isolates and purifies the protein by a simple process. Accordingly, the method according to the present invention highly pure interleukin-2, and thus has a significant effect on the mass-production of interleukin-2.

11 Claims, 6 Drawing Sheets
Specification includes a Sequence Listing.

METHOD FOR PRODUCING INTERLEUKIN-2 PROTEIN USING METHYLOTROPHIC YEAST

REFERENCE TO SEQUENCE LISTING SUBMITTED ELECTRONICALLY VIA EFS-WEB

The content of the electronically submitted sequence listing (Name: 19716-0030001_ST25.txt; Size: 33,916 bytes; and Date of Creation: Sept. 5, 2017) is incorporated by reference in its entirety.

TECHNICAL FIELD

The present invention relates to a method for producing interleukin-2 protein using methylotrophic enzyme.

BACKGROUND ART

The medical proteins or industrial enzymes useful for humans, which could only be obtained in a trace amount from the natural state in the past, could be mass-produced by the development of recombinant DNA technology. For example, *E. coli* cells have been most widely used as host cells to produce large amounts of such useful proteins, and useful recombinant proteins, including hormones such as insulin and β-endorphin, and immunomodulators such as interferon, have been researched and developed.

To efficiently produce recombinant proteins, selection of suitable host cells is very important. As host cells for producing therapeutic recombinant proteins, various host systems, including microbial, plant and animal cells, have been developed and used. Particularly, for most glycoproteins, animal cells that are higher eukaryotic cells have been used as host cells. However, animal cells have shortcomings in that they are cultured using expensive media, show low protein production yields, and are cultured under strict conditions. For this reason, for non-glycoproteins, microorganisms are used as hosts.

Among various microbial host systems, *E. coli* and yeast are mainly used as primary host cells for producing large amounts of recombinant proteins. These microbial expression systems have advantages over higher eukaryotic cell expression systems in that the production cost is low and the production process is simple. However, there is a limit to the production of either glycoproteins that require post-translational modification such as glycosylation to have activity, or proteins having a very large and complex structure. Furthermore, when a useful protein is expressed in yeast, an insoluble inclusion body protein is formed which lost its activity by various mechanisms without being completely folded. Although this insoluble protein may be easily isolated in an initial stage to provide a highly pure protein in some cases, it lacks activity as the protein. For this reason, complex and costly denaturation and refolding processes are required to obtain a biologically active soluble protein from the insoluble protein.

Furthermore, even if cell lines for producing recombinant protein drugs are established, studies on processes for production of recombinant proteins are required to identify quality and characteristics for cell lines, and the development of scale-up production processes is also required. The protein production processes are largely divided into an upstream process of establishing a host cell line, a midstream process of culturing the cell line to produce a large amount of recombinant protein, a downstream process for separation and purification, and a process of formulating a purified drug substance with an excipient or the like. For each of such unit processes, optimal conditions for key process parameters need to be established, thereby establishing optimal production process conditions.

Meanwhile, interleukin-2 consists of 153 amino acids and is produced mainly by T cells expressing the surface antigen CD4. Transformed T cells, B cells, lymphocytic cancer cells, LAK cells and NK cells also secrete interleukin-2. It is known that the production of interleukin-2 is induced by mitogen- or allergen-mediated activation of T cells, and several kinds of secondary stimulations are required to maximize the production of interleukin-2, but resting cells cannot produce interleukin-2. It has been reported that interleukin-2 and its receptor are associated with many diseases. However, studies on the molecular characteristics of interleukin-2 and its receptor have been very limited, because they are obtained in limited amounts.

For example, many methods have been studied to increase immunity against cancer by administration of functional interleukin-2 gene, and thus studies on interleukin-2 and the demand for interleukin-2 as a therapeutic agent have continued to increase. However, technology for producing a large amount of interleukin-2 is still insufficient.

Under this background, there is a need for studies on an optimized method for producing a large amount of interleukin-2 using a microbial expression system.

DISCLOSURE

Technical Problem

It is an object of the present invention to provide a method for producing interleukin-2, comprising the steps of:
(a) cloning an interleukin-2 expression construct for yeast, wherein the expression construct comprises a methanol oxidase (MOX) promoter, a human serum albumin gene or a fragment thereof, and an interleukin-2 gene;
(b) transforming yeast host cells with the expression construct prepared in step (a), and culturing the transformed yeast cells to express interleukin-2; and
(c) isolating the expressed interleukin-2 from the transformed yeast cells cultured in step (b).

Another object of the present invention is to provide a method for producing interleukin-2, comprising the steps of:
(a) culturing *Hansenula polymorpha* transformed with an interleukin-2 expression construct for yeast, wherein the expression construct comprises a methanol oxidase (MOX) promoter, a human serum albumin gene or a fragment thereof, a tobacco etch virus protease site, and an interleukin-2 gene;
(b) isolating a protein from the culture of step (a); and
(c) treating the isolated protein of step (b) with tobacco etch virus protease to separate interleukin-2.

Technical Solution

To achieve the above objects, the present inventors have examined the expression levels of interleukin-2 depending on culture conditions by culture of a methylotrophic yeast transformed with a recombinant vector comprising human serum albumin and interleukin-2 gene sequences, and have established culture conditions for producing a large amount of interleukin-2, thereby completing the present invention.

The present invention provides a method for producing interleukin-2, comprising the steps of:

(a) cloning an interleukin-2 expression construct for yeast, wherein the expression construct comprises a methanol oxidase (MOX) promoter, a human serum albumin gene or a fragment thereof, and an interleukin-2 gene;

(b) transforming yeast host cells with the expression construct prepared in step (a), and culturing the transformed yeast cells to express interleukin-2; and (c) isolating the expressed interleukin-2 from the transformed yeast cells cultured in step (b).

The method for producing interleukin-2 according to the present invention comprises step (a) of cloning an interleukin-2 expression construct for yeast, wherein the expression construct comprises a methanol oxidase (MOX) promoter, a human serum albumin gene or a fragment thereof, and an interleukin-2 gene.

The interleukin-2 expression construct for yeast, which is prepared in step (a), is inducibly expressed by a carbon source related to methanol metabolism, and may be used to produce a large amount of interleukin-2 at low costs.

As used herein, the term "expression construct" means a nucleic acid molecule that comprises only the minimum elements for intracellular protein expression.

The expression construct that is used in the present invention may be a recombinant vector. Preferably, it may be a vector constructed according to a recombinant vector construction method known in the art. Specifically, it may be a vector obtained by linking the methanol oxidase (MOX) promoter upstream of the full-length sequence of the human serum albumin gene or a fragment thereof, and linking the linked promoter upstream of the interleukin-2 gene. For example, a pYHSA13 (T-1) vector comprises: an MOX promoter which is the methanol inducible promoter of *Hansenula polymorpha*; an ampicillin-resistant gene which is a selectable marker for *E. coli*; leu which is a marker gene for *Hansenula polymorpha*; and a human serum albumin (HSA) gene which is expressed and secreted by the MOX promoter. Of the cleaved sequences of the pYHSA13 (T-1) vector, the nucleotide sequence comprising human serum albumin may be ligated into the high-copy vector pUC18 for *E. coli* to obtain a recombinant vector (pUC18-HSA), and interleukin-2 may be cloned into the recombinant vector (pUC18-HSA), thereby constructing a recombinant vector for fusion expression. FIG. 1 shows a schematic view of the pUC18-HSA recombinant vector.

In the present invention, the methanol oxidase (MOX) promoter is a promoter derived from the genomic DNA of *Hansenula polymorpha*. The MOX promoter that is used in the present invention is a strong promoter that easily controls expression, and can be integrated into multiple sites on each chromosome. Thus, an expression vector comprising the methanol oxidase (MOX) promoter is highly stable in a long-term culture process performed using a non-selective medium. Accordingly, the MOX promoter is very effectively used for expression of interleukin-2. The MOX promoter that is used in the present invention may have a nucleotide sequence of SEQ ID NO: 1. In addition, nucleotide sequences, which have properties functionally equivalent to the nucleotide sequence of SEQ ID NO: 1 and have a sequence homology of 90%, 91%, 92%, 93%, 94%, 95%, 96%, 97%, 98%, 99% or more to the nucleotide sequence of SEQ ID NO: 1, also fall within the scope of the present invention.

As used herein, the expression "human serum albumin gene or a fragment thereof" refers to either a gene encoding a molecular weight 65-kDa protein consisting of 585 amino acids, which is produced in the liver and secreted into blood, or a fragment of a gene encoding human serum albumin. The human serum albumin gene or a fragment thereof, which is used in the present invention, encodes a protein having a secretory signal sequence, and is easily secreted by itself without requiring a secretory system. Particularly, when the human serum albumin protein is used as a fusion protein with interleukin-2 in expression of interleukin-2 whose expression and secretion expression is not easy due to its large size or complex structure, it significantly increases the expression and secretion of interleukin-2. In the present invention, the human serum albumin gene has a nucleotide sequence of SEQ ID NO: 2. In addition, nucleotide sequences, which have properties functionally equivalent to the nucleotide sequence of SEQ ID NO: 2 and have a sequence homology of 90%, 91%, 92%, 93%, 94%, 95%, 96%, 97%, 98%, 99% or more to the nucleotide sequence of SEQ ID NO: 2, also fall within the scope of the present invention. Furthermore, the fragment of the human serum albumin gene is a portion of the human serum albumin gene that may be secreted by itself without requiring a secretory system, and may have a nucleotide sequence encoding an amino acid sequence consisting of 100, 200, 300, 400, 500 or more amino acids counted from the N-terminus of the full-length amino acid sequence of human serum albumin. Preferably, the fragment of the human serum albumin gene has a nucleotide sequence of SEQ ID NO: 3.

In the present invention, interleukin-2 is a protein consisting of 153 amino acids, which is produced mainly by T cells expressing the surface antigen CD4. The interleukin-2 gene that is used in the present invention has a nucleotide sequence of SEQ ID NO: 4. In addition, nucleotide sequences, which have properties functionally equivalent to the nucleotide sequence of SEQ ID NO: 4 and have a sequence homology of 90%, 91%, 92%, 93%, 94%, 95%, 96%, 97%, 98%, 99% or more to the nucleotide sequence of SEQ ID NO: 4, also fall within the scope of the present invention.

The expression construct of the present invention is used in yeast. Preferably, the yeast is a methylotrophic yeast. More preferably, the yeast is *Hansenula polymorpha, Pichia pastoris, Candia boidini, Pichia methanolica*, or *Ogataea minuta*. Even more preferably, the yeast is *Hansenula polymorpha*.

The interleukin-2 expression construct for yeast according to the present invention may further comprise, between the human serum albumin gene sequence and the interleukin-2 gene sequence, a sequence that can be cleaved by protease so as to recover only the IL-2 sequence after production of a fusion protein by the expression construct. As used herein, the term "protease" refers to an enzyme that cleaves the peptide bonds of amino acids. The protease may be, for example, serine protease, threonine protease, cysteine protease, aspartate protease, metalloprotease, glutamic acid protease, or a combination of two or more thereof. In addition, the protease may be, for example, TEV (tobacco etch virus) protease, trypsin, chymotrypsin, elastase, pepsin, enteropeptidase, or a combination of two or more thereof. Regions that can be cleaved by enzymes may vary depending on the kind of enzyme, and are known to those skilled in the art. In the present invention, a sequence that can be cleaved by the protease is the tobacco etch virus protease site that can be cleaved by tobacco etch virus protease and that has a nucleotide sequence of SEQ ID NO: 5.

The expression construct according to the present invention further comprises restriction enzyme recognition nucleotide sequences that enable a foreign protein-encoding nucleotide sequence to be cloned so as to be operably linked to the promoter sequence.

Restriction enzymes that are recognized by the restriction enzyme recognition nucleotide sequences contained in the expression construct of the present invention are not particularly limited. Examples of the restriction enzymes include, but are not limited to, EcoRV, NheI, NotI, SphI, XbaI and the like. Preferably, the restriction enzymes may be EcoRV and NheI.

The expression construct that is used in the present invention comprises a transcription terminator sequence. For example, the expression construct comprises a polyadenylation sequence for transcriptional termination. For example, the expression construct comprises a bovine growth hormone terminator, an SV40-derived polyadenylation sequence, β-globin polyA, HSV TK polyA or MOX terminator, but is not limited thereto.

In addition, the expression construct according to the present invention may comprise, as a selectable marker, an antibiotic-resistant gene that is generally used in the present invention. For example, the expression construct comprises a gene resistant to ampicillin, gentamicin, carbenicillin, chloramphenicol, streptomycin, kanamycin, geneticin (G418), neomycin or tetracycline.

The expression construct according to the present invention may further comprise, in addition to the above-described elements, functional connections operably linked to a nucleic acid expression regulatory sequence capable of regulating the transcription and/or translation of the nucleic acid sequence.

The expression construct according to the present invention is preferably an expression construct shown in FIG. 3(a) or 3(b). More preferably, the expression construct is an expression construct shown in FIG. 3(a). According to one embodiment of the present invention, the expression construct has a nucleotide sequence of SEQ ID NO: 6 or SEQ ID NO: 7.

In the present invention, cloning may be performed using any method known in the art. For example, the interleukin-2 gene and the expression construct according to the present invention are treated with restriction enzymes, and then the interleukin-2 gene is stably inserted into the expression construct by a suitable enzyme, for example, ligase.

The method for producing interleukin-2 according to the present invention comprises step (b) of transforming yeast host cells with the expression construct prepared in step (a), and culturing the transformed yeast cells to express interleukin-2.

The yeast that is used in the present invention is as described above. The transformed yeast is preferably a transformant of *Hansenula polymorpha*. More preferably, the transformed yeast is transformed *Hansenula polymorpha* deposited under accession number KCTC18329P on Oct. 1, 2014 at the Korean Collection for Type Cultures, and converted on Dec. 14, 2018 to a deposit under the Budapest Treaty at the Korean Collection for Type Cultures as accession number KCTC 13777BP.

In the present invention, a method of transforming yeast cells with the expression construct may be performed using a method of transforming eukaryotic cells with a vector as known in the art. Examples of the method for transformation include microinjection, calcium phosphate precipitation, electroporation, liposome-mediated transfection, DEAE-dextran treatment, gene bombardment, and acetic-lithium DMSO methods.

In the present invention, culture of the transformed yeast may be performed according to a conventional method known in the art. However, culture of the transformed yeast shows high cell growth and protein production under the conditions as described below.

A culture medium that is used in the present invention may be a methanol-containing medium. Example of the medium include YPM (2% (w/v) bacto-peptone, 1% (w/v) bacto-yeast extract, 3% (w/v) methanol) medium, YPD (2% (w/v) bacto-peptone, 1% (w/v) bacto-yeast extract, 2% (w/v) D-glucose) medium, minimal medium YNBD (0.67% (w/v) YNB without amino acids, amino acid mixture, 2% (w/v) D-glucose) and the like. Preferably, the medium is YPM medium.

In the present invention, a carbon source for culture is preferably methanol. The concentration of methanol is 1% (w/v) to 10% (w/v), preferably 2% (w/v) to 5% (w/v), more preferably 2% (w/v) to 4% (w/v).

In the present invention, the culturing is performed at a temperature of 25 to 45° C., preferably 30 to 40° C., more preferably 35 to 39° C.

In the present invention, the pH of the culture is 4.5 to 7.0, preferably 5.0 to 6.5, more preferably 5.7 to 6.3.

In the present invention, the shaking speed of the culture is 100 to 300 rpm, preferably 150 to 250 rpm, more preferably 180 to 220 rpm.

The method for producing interleukin-2 according to the present invention comprises step (c) of isolating the expressed interleukin-2 from the transformed yeast cells cultured in step (b).

The method according to the present invention may comprise a protein concentration step known in the art in order to isolate interleukin-2. For example, the interleukin-2 protein may be recovered by treatment with sodium deoxycholate (Na-DOC) and trichloroacetic acid (TCA), centrifugation and sonication, or may be isolated by precipitation with ammonium sulfate. In addition, another method may be used which comprises separating proteins according to size by removing proteins smaller than the molecular weight of the target protein by use of a spin column such as Amicon Ultra (Milipore).

For isolation of a fusion protein of interleukin-2 and human serum albumin, the interleukin-2 expression construct that is used in the present invention may further comprise, between the human serum albumin gene sequence and the interleukin-2 gene sequence, a sequence that can be cleaved by protease in order to recover only the IL-2 sequence. Thus, the method according to the present invention may further comprise, before the isolating step, a step of treatment with protease. The protease is as described above, and treatment with the protease may be performed at a temperature of 25 to 37° C. for 1-12 hours. When the expression construct comprise a TEV protease site, treatment with TEV protease may preferably be performed at a temperature of 28 to 32° C. for 4 to 8 hours, thereby isolating the fusion protein.

In the present invention, isolation of the expressed interleukin-2 from the cultured transformed yeast cells may be performed using an isolation and purification method that is generally used in the art. For example, various methods may be used, including solubility fractionation using ammonium sulfate or PEG, ultrafiltration based on molecular weight, and various chromatographic techniques (based on size, charge, hydrophobicity or affinity). Usually, a combination of the above-mentioned methods is used for isolation and purification.

The present invention also provides a method for producing interleukin-2 using *Hansenula polymorpha*, the method comprising the steps of:

(a) culturing *Hansenula polymorpha* transformed with an interleukin-2 expression construct for yeast, wherein the expression construct comprises a methanol oxidase (MOX) promoter, a human serum albumin gene or a fragment thereof, a tobacco etch virus protease site, and an interleukin-2 gene;

(b) isolating a protein from the culture of step (a); and (c) treating the isolated protein of step (b) with tobacco etch virus protease to separate interleukin-2.

The method for producing interleukin-2 according to the present invention comprises step (a) of culturing *Hansenula polymorpha* transformed with an interleukin-2 expression construct for yeast, wherein the expression construct comprises a methanol oxidase (MOX) promoter, a human serum albumin gene or a fragment thereof, a tobacco etch virus protease site, and an interleukin-2 gene.

The interleukin-2 expression construct for yeast, which is used in the present invention, may be prepared by the above-described method.

The transformed *Hansenula polymorpha* may be the yeast transformed according to the above-described method. Preferably, the transformed *Hansenula polymorpha* is transformed *Hansenula polymorpha* deposited under accession number KCTC18329P on Oct. 1, 2014 at the Korean Collection for Type Cultures, and converted on Dec. 14, 2018 to a deposit under the Budapest Treaty at the Korean Collection for Type Cultures as accession number KCTC 13777BP.

Culture of the transformed *Hansenula polymorpha* shows high cell growth and protein production under the conditions as described below.

A culture medium that is used in the present invention may be a methanol-containing medium. Example of the medium include YPM (2% (w/v) bacto-peptone, 1% (w/v) bacto-yeast extract, 3% (w/v) methanol) medium, YPD (2% (w/v) bacto-peptone, 1% (w/v) bacto-yeast extract, 2% (w/v) D-glucose) medium, minimal medium YNBD (0.67% (w/v) YNB without amino acids, amino acid mixture, 2% (w/v) D-glucose) and the like. Preferably, the medium is YPM medium.

In the present invention, a carbon source for culture is preferably methanol. The concentration of methanol is 1% (w/v) to 10% (w/v), preferably 2% (w/v) to 5% (w/v), more preferably 2% (w/v) to 44 (w/v).

In the present invention, the culturing is performed at a temperature of 25 to 45° C., preferably 30 to 40° C., more preferably 35 to 39° C.

In the present invention, the pH of the culture is 4.5 to 7.0, preferably 5.0 to 6.5, more preferably 5.7 to 6.3.

In the present invention, the shaking speed of the culture is 100 to 300 rpm, preferably 150 to 250 rpm, more preferably 180 to 220 rpm.

The method for producing interleukin-2 according to the present invention comprises step (b) of isolating a protein from the culture of step (a).

To isolate the interleukin-2 protein from the culture, the protein may be concentrated according to a method known in the art. For example, only the protein may be extracted by treatment with sodium deoxycholate (Na-DOC) and trichloroacetic acid (TCA), centrifugation and sonication.

The method for producing interleukin-2 according to the present invention comprises step (c) of treating the isolated protein of step (b) with tobacco etch virus protease to isolate interleukin-2.

For isolation of a fusion protein of interleukin-2 and human serum albumin gene, treatment with TEV protease may be performed to cleave the TEV protease site added between the human serum albumin and interleukin-2 gene sequences. Treatment with the TEV protease may be performed at a temperature of 28 to 32° C. for 4 to 8 hours.

Isolation of the expressed interleukin-2 from the cultured transformed yeast cells may be performed using an isolation and purification method that is generally used in the art. For example, various methods may be used, including solubility fractionation using ammonium sulfate or PEG, ultrafiltration based on molecular weight, and various chromatographic techniques (based on size, charge, hydrophobicity or affinity). Usually, a combination of the above-mentioned methods is used for isolation and purification.

Advantageous Effects

The method for producing interleukin-2 according to the present invention shows high cell growth and protein synthesis rates by use of the established optimal cell line, and produces a large amount of a protein comprising interleukin-2 by use of the established optimal culture conditions utilizing methanol that is an inexpensive carbon source. In addition, the method according to the present invention isolates and purifies the protein by a simple process. Accordingly, the method according to the present invention highly pure interleukin-2, and thus has a significant effect on the production of interleukin-2.

MODE FOR INVENTION

The advantages and features of the present invention, and the way of attaining them, will become apparent with reference to the examples described below. However, the present invention is not limited to the examples disclosed below and can be embodied in a variety of different forms. Rather, these examples are provided so that this disclosure will be thorough and complete, and will fully convey the scope of the present invention to those skilled in the art. The scope of the present invention will be defined by the appended claims.

EXAMPLE 1

Construction of Human Serum Albumin/Interleukin-2 Fusion Expression Vector and Transformed Strains To obtain a vector set for *Hansenula polymorpha*, which can express and secrete HSA-IL-2 fusion proteins, by use of two human serum albumin (HSA) gene fragments having different sizes, a pYHSA13 (T-1) vector for *H. polymorpha*, which has a His-tag attached to the C-terminus of HSA gene, and a pUC18 vector (Invitrogen) which is a high-copy vector for *B. coli*, were used. Herein, the pYHSA13 (T-1) vector comprises: a MOX promoter which is the methanol inducible promoter of *H. polymorpha*; an ampicillin-resistant gene which is a selectable marker for *E. coli*; leu which is a marker gene for *H. polymorpha*; and a HSA gene which is expressed and secreted by the MOX promoter.

Figure 1:
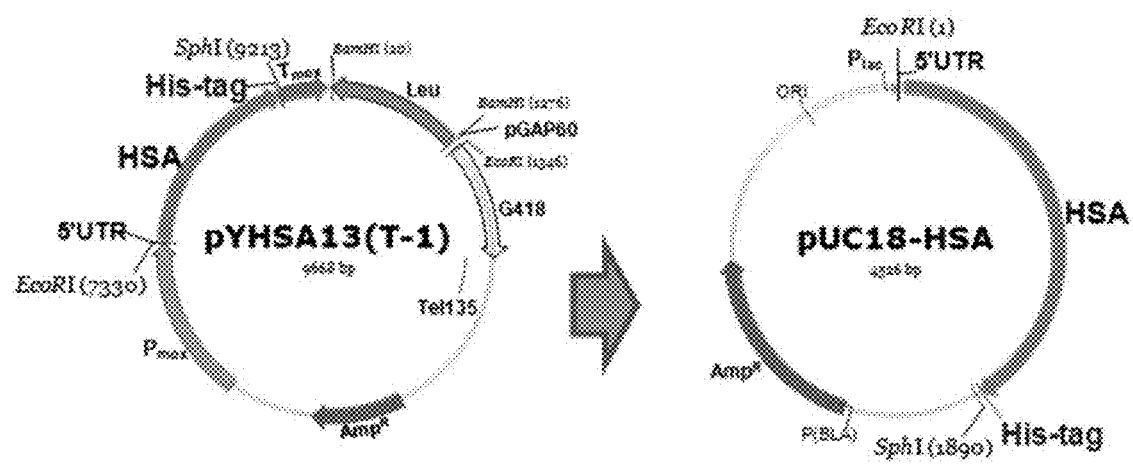
FIG. 1 shows schematic views of a pYHSA13 (T-1) vector and a pUC18-HSA vector.

The pYHSA13 (T-1) vector was cleaved with EcoRI and BamHI to obtain three vector fragments. Among the vector fragments, a 1.8-kb fragment comprising the HSA (His-tag) gene from the 5'-UTR of the vector was subcloned into a pUC18 vector that is a high-copy vector for *E. coli*, thereby constructing a pUC18-HSA vector. Schematic views of the pYHSA13 (T-1) vector and the pUC18-HSA vector are shown in FIG. 1.

To perform a series of genetic engineering operations for introducing functional domains, long primers having a tag length of 50-mer or more were used. In the first PCR, a functional domain linker and a Strep-tag sequence were constructed using HpaI-tagged primers, and in the second PCR, a multiple cloning site and a Tev sequence were constructed using NheI-tagged primers, and the first primer tag HpaI sequence was removed. Finally, in the third PCR, a HpaI recognition sequence was made between the HSA fragment and the His-tag sequence, followed by linkage with 6×His. The primer sequences used in the PCR are shown in Table 1 below.

TABLE 1

Primer sequences

| Primers | Sequences |
|---|---|
| TAG-d1 (SEQ ID NO: 8) | TTTGTTAACCACCCGCAGTTGGAAAAGTGACCCGGG AAGCTTGGCACTGGCCGT |
| TAG-d2 (SEQ ID NO: 9) | AAAGCTAGCGGCCGCGATATCTGGAGCCACCCGCAG TTCGAAAAG |
| TAG-u2 (SEQ ID NO: 10) | GTGGCTAGCGCCCTGAAAATACAGGTTTTCGGATCC ACCGCCACCCCAGCC |
| HSA-F (SEQ ID NO: 11) | CTCAAGCTTGAATTCGGCACG |
| HSA-u1 (SEQ ID NO: 12) | TTTGTTAACGGGGGAGATTTGGATTGTCATCTTT |
| HSA-u5 (SEQ ID NO: 13) | TTTGTTAACTAAGCCTAAGGCAGCTTGACTTGCAGC |

Figure 2:
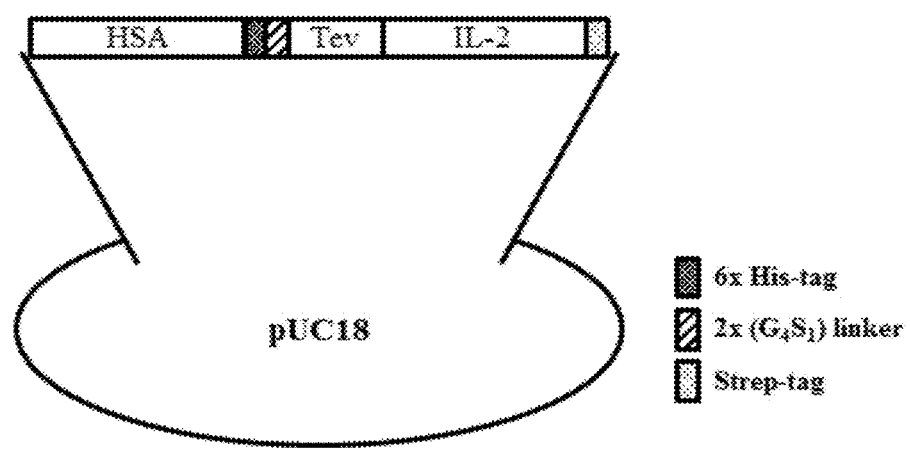
FIG. 2 shows a schematic view of a PUC-HSA-IL-2 vector comprising IL-2.

The IL-2 gene was cloned into the pUC18-HSA vector, thereby constructing a fusion expression vector enabling a HSA/IL-2 fusion protein to be efficiently expressed and secreted. In order to enable the expressed and secreted fusion protein to be effectively separated, HSA-His tag and IL-2-Strep tag binding sites were inserted into the fusion expression vector, and a TEV protease site for recovering only the IL-2 protein after expression and secretion was attached between the HSA and IL-2 genes. A schematic view of the fusion expression vector is shown in FIG. 2.

Figure 3:
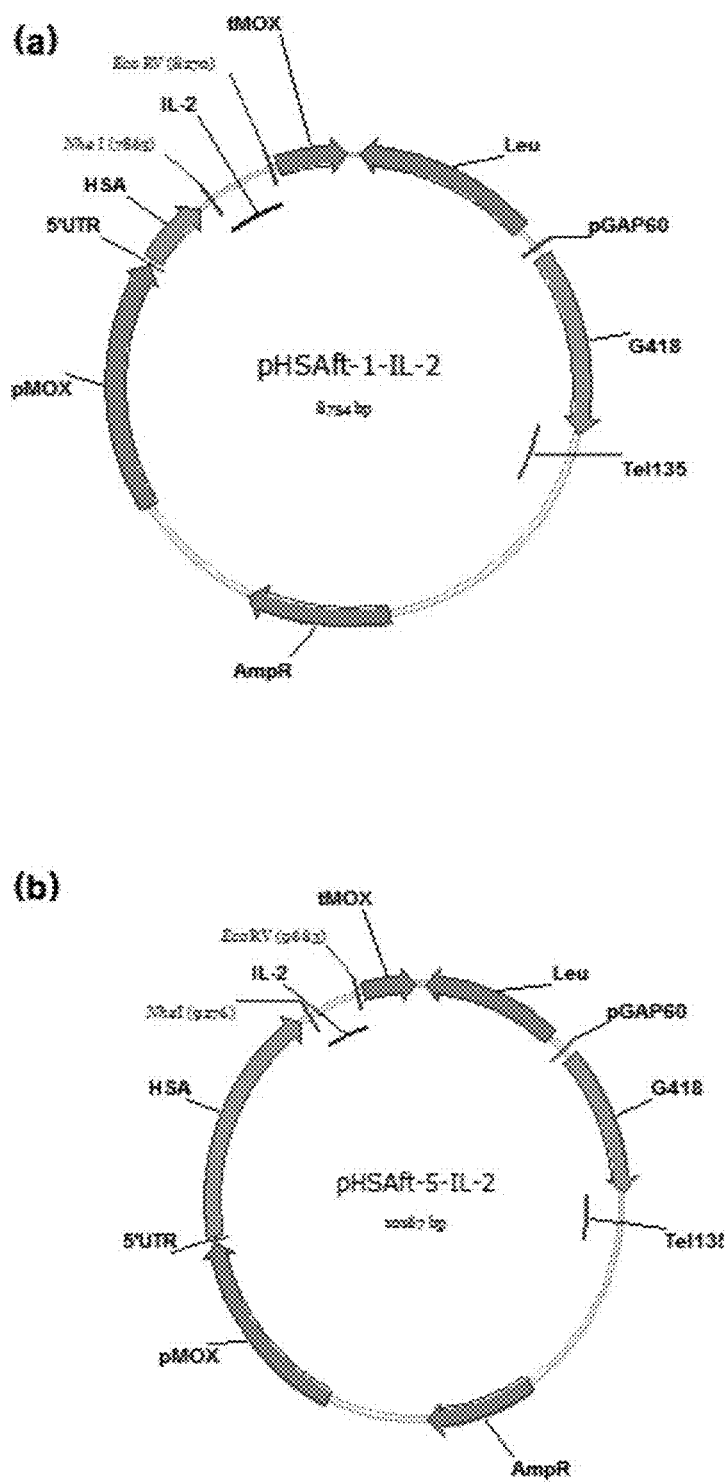
FIG. 3 shows schematic views of the specific configurations of pHSAft-5-IL-2 and pHSAft-1-IL-2 vectors.

In order to construct the HSA/IL-2 fusion expression vector enabling secretion of the IL-2 protein to be efficiently induced, each of the full-length sequence of the HSA gene and the 137-amino acid fragment sequence in front of thereof was linked upstream of the IL-2 gene, thereby constructing pHSAft-5-IL-2 and pHSAft-1-IL-2 vectors enabling HSA and IL-2 to be expressed and secreted as a fusion protein. The specific configurations of the vectors are shown in FIGS. 3(a) and 3(b), respectively. The sequences of the pHSAft-5-IL-2 and pHSAft-1-IL-2 vectors are shown by SEQ ID NOs: 6 and 7, respectively. In the process of performing PCR using as a template the pUC18-HSA vector having the functional domains introduced therein, different reverse primers were used to construct two HSA fusion tag domains having different sizes. HSA cleavage sites were determined based on the three-dimensional structure of HSA, and the desired DNA fragments were obtained by PCR and cloned upstream of the functional domain. Using the same, vectors for expressing the fusion protein were constructed. The primer set used in the PCR is shown in Table 2 below.

TABLE 2

Primer sequence

| Primers | Sequences |
|---|---|
| IL-2-F (SEQ ID NO: 14) | CTAGCTAGCATGCCTACTTCAAGTTCTAC |
| IL-2-R (w/His tag) (SEQ ID NO: 15) | GCTTGATATCTCAGTGGTGGTGGTGGTGA GTCAGTGTTGAGATG |

To perform transformation using the constructed pHSAft-5-IL-2 and pHSAft-1-IL-2 vectors, *H. polymorpha* DL1-L precultured in YPD (2% (w/v) bacto-peptone, 1% (w/v) bacto-yeast extract, and 2% (w/v) D-glucose) liquid medium was adjusted to an initial OD600 value of 0.2 in a 500-ml baffled flask, and 50 ml of the strain was cultured at 180 rpm in a shaking incubator at 30° C. The strain was cultured for 6-7 hours until the OD600 value reached 1.0. Next, the culture was centrifuged at 4,000 rpm for 10 minutes at 4° C. The supernatant was removed, and the pellet was suspended by pipetting in 1 ml of LiAc/TE buffer (0.01 M Tris-HCl, 1 mM EDTA, 0.1M LiAc, pH 7.5). The suspension was centrifuged at 13,000 rpm for 1 minute to obtain a precipitate. Then, the pellet was suspended again in 500 μl of LiAc/TE buffer to prepare competent cells. The cell suspension was dispensed into five tubes (100 μl for each tube), and 2 μl of the recombinant vector, 10 μl of salmon sperm DNA, and 600 μl of PEG/LiAc buffer (50% polyethylene glycol, 0.01 M Tris-HCl, 1 mM EDTA, 0.1M LiAc, pH 7.5) were added to each of the tubes, and then carefully pipetted about 3-4 times. Each tube was allowed to stand at 30° C. for 30 minutes, and then 70 μl of DMSO was added thereto, following by slight pipetting. Next, the content in each tube was heat-treated at 42° C. for 15 minutes. Each tube was allowed to stand on ice for 3 minutes, followed by centrifugation at 13,000 rpm for 1 minute. The obtained precipitate was suspended in sterile distilled water, and the suspension was smeared on selective medium SC-Leu (0.67% yeast nitrogen base w/o amino acids, Leu-dropout supplement, 2% glucose, 2% agar) and incubated at 37° C. for 48 hours, thereby obtaining transformants.

EXAMPLE 2

Screening of Recombinant Strains

The pHSAft vector comprises the secretory signal sequence of HSA protein attached thereto to efficiently increase the secretion of IL-2 protein, and induces HSA and IL-2 to be expressed and secreted as a fusion protein. The difference between the pHSAft-1-IL-2 vector comprising a 137-amino-acid fragment of HSA and the pHSAft-5-IL-2 vector comprising the full-length (608-amino-acid) region of HSA is only a difference in the length of HSA, and the two vectors were constructed so as to enable the IL-2 protein to be secreted.

Using the transformed strain *H. polymorpha* (pHSAft-1-IL-2) and *H. polymorpha* (pHSAft-5-IL-2) constructed in Example 1, a screening experiment was performed. Each of the two transformants was plated on SC-Leu selective medium (0.67% yeast nitrogen base w/o amino acids, Leu-dropout supplement, 2% glucose, 2% agar) and incubated for 30 hours. Then, eight of the grown colonies for each transformant were selected and named "*H. polymorpha* (pHSAft-1-IL-2) B1-8" and "*H. polymorpha* (pHSAft-5-IL-2) R1-8", respectively. A screening experiment was performed to screen strains showing the best cell growth and protein production.

Each of a total of 16 strains (B1-8 and R1-8) was inoculated in YPM medium (2% (w/v) bacto-peptone, 1% (w/v) bacto-yeast extract, 3% (w/v) methanol), and inoculated in a shaker [SI-300R, Lab Companion] for 30 hours under the conditions of 1% seed volume, 37° C. and 200 rpm.

Cell growth (OD600) was measured using a spectrophotometer [UV1240, SHIMADZU]. When the OD600 value exceeded 1.0, each strain was diluted properly and incubated for 30 hours, followed by measurement of the final OD value of each strain, thereby determining the degree of culture of each strain.

In order to quantify the amount of protein produced by each recombinant strain, the culture was cooled on ice, and then 2% sodium deoxycholate (Na-DOC) was added thereto to a final concentration of 0.02% and concentrated. 50% trichloroacetic acid (TCA) was mixed thereto to a final concentration of 7.5%, and then the sample was allowed to stand on ice for 2 hours. Next, the cooled sample was centrifuged in Centrifuge Combi-514R at 4,000 rpm for 30 minutes at 4° C., after which the supernatant was removed, and 2 ml of tetrahydrofuran (THF) was added to the precipitate. Next, the suspension was centrifuged at 4,000 rpm for 30 minutes at 4° C., after which the supernatant was removed, and tetrahydrofuran (THF)-added precipitate was removed again in the bath sonication (Powersonic 520, Hwashin Tech, Korea). The sample having the same volume as BSA standard solution 50 was prepared in a micro tube, and Brilliant Blue G-250 950 was added thereto, after which the sample was incubated at room temperature for 5 minutes, followed by measurement of the OD at 595 nm.

The results of the measurement are shown in Tables 3 and 4 below.

TABLE 3

Growth and protein growth of *H. polymorpha* (pHSAft-1-IL-2) strain (*average values)

| Strains | Cell growth* (OD) | Total proteins* (µg/ml) |
|---|---|---|
| B1 | 5.22 | 2.09 |
| B2 | 5.22 | 2.09 |
| B3 | 5.33 | 2.10 |
| B4 | 4.86 | 1.28 |
| B5 | 3.77 | 1.19 |
| B6 | 5.42 | 2.15 |
| B7 | 5.40 | 2.14 |
| B8 | 5.45 | 2.16 |

TABLE 4

Growth and protein growth of *H. polymorpha* (pHSAft-5-IL-2) strains (*average values)

| Strains | Cell growth* (OD) | Total proteins* (µg/ml) |
|---|---|---|
| R1 | 4.29 | 1.08 |
| R2 | 4.44 | 1.15 |
| R3 | 4.52 | 1.16 |
| R4 | 5.41 | 2.13 |
| R5 | 5.34 | 2.10 |
| R6 | 3.94 | 1.20 |
| R7 | 5.21 | 2.09 |

As can be seen in Table 3 above, among the eight *H. polymorpha* (pHSAft-1-IL-2) strains (B1-B8) comprising a fragment of the human Serum albumin gene, the B8 strain showed values of OD 5.45 in cell growth and 2.16 µg/ml in total protein production, suggesting that the B8 strain is the best strain.

In addition, as can be seen in Table 4 above, among the eight *H. polymorpha* (pHSAft-5-IL-2) strains (R1-R8) comprising the full-length sequence of the human serum albumin gene, the R4 strain showed values of OD 5.41 in cell growth and 2.13 g/ml in total protein production, suggesting that the R4 strain is the best strain.

Generally, it was shown that cell growth and total protein production were higher in the *H. polymorpha* (pHSAft-1-IL-2) strains than in the *H. polymorpha* (pHSAft-5-IL-2) strains.

Among the *H. polymorpha* (pHSAft-1-IL-2) strains that produce recombinant interleukin-2, the B8 strain was finally selected. The selected B8 strain was deposited in the Korean Collection for Type Cultures (KCTC) at the Korean Research Institute of Bioscience and Biotechnology (KRIBB) on Oct. 1, 2014 and assigned accession number KCTC 18329P and converted on Dec. 14, 2018 to a deposit under the Budapest Treaty at the Korean Collection for Type Cultures as accession number KCTC 13777BP.

EXAMPLE 3

Examination of Secretory Expression of Protein and Separation of Fusion Protein Cells obtained by culturing the transformant in YPD liquid medium was adjusted to an OD600 of 0.1 and transferred into an E-tube in an amount suitable for seeding into YPM liquid medium. Then, the cells were centrifuged at 13,000 rpm for 1 minute. The precipitate was added with 1 ml of sterile distilled water, suspended by pipetting, and the suspension was centrifuged at 13,000 rpm for 1 minute to obtain the precipitate. The pellet was suspended and inoculated in YPM liquid medium to induce protein expression.

To concentrate the expressed and secreted protein, 2% sodium deoxycholate (Na-DOC) was added to a final concentration of 0.02%. 50% trichloroacetic acid (TCA) was added to a final concentration of 7.5%, and then the sample was allowed to stand on ice for 2 hours. Then, the sample was centrifuged at 4,000 rpm (Centrifuge Combi-514R) for 30 minutes at 4° C., after which the supernatant was removed, and the precipitate was added in 2 ml of tetrahydrofuran (THF). The suspension was centrifuged at 4,000 rpm for 30 minutes at 4° C., after which the supernatant was removed, and tetrahydrofuran (THF)-added precipitate was removed again in the bath sonication (Powersonic 520, Hwashin Tech, Korea).

In order to separate the expressed and secreted fusion protein, components were collected using ProTEV Plus (Promega, USA). Next, the sample was incubated in an incubator at 30° C. for 6 hours and kept at −20° C.

The prepared protein sample was electrophoresed on SDS-PAGE gel, and the gel was transferred onto a PVDF membrane (Bio-Rad) which was then assembled with a transfer caster, filled with transfer buffer (192 mM glycine, 25 mM Tris, 20% methanol), and kept at 80 V for 1 hour. Next, the PVDF membrane was placed in blocking buffer [5% skim milk, TBST (20 mM Tris-HCl, 150 mM NaCl, 0.05% Tween20)] and incubated with shaking at room temperature for about 1 hour to prevent nonspecific binding. Next, the PVDF membrane was incubated with primary antibody in blocking buffer for about 1 hour and 30 minutes, and then washed three times with TBST buffer for 10 minutes each time. Next, the secondary antibody was added to the blocking buffer, and shaken at room temperature for about 1 hour, and then washed three times with TBST buffer for 10 minutes each time. Thereafter, solution A and solution B of an ECL (enhanced chemiluminescence) kit were mixed at 1:1 ratio and added to the PVDF membrane which was then incubated for 1 minute to induce color development. Then, the PVDF membrane was exposed to X-ray film to detect a signal.

Figure 4:
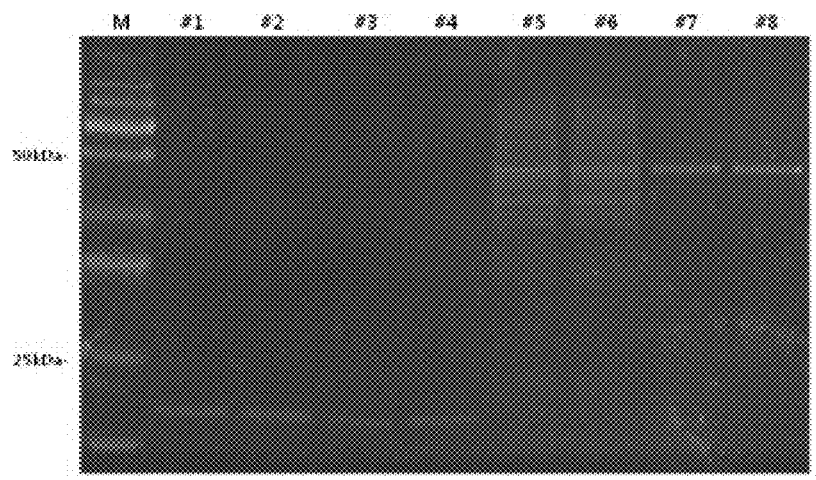
FIG. 4 shows the results of examining the expression and secretion of an HSA-IL2 fusion protein and interleukin-2 from *H. polymorpha* transformed with a pHSAft-5-IL-2 vector.
Figure 5:
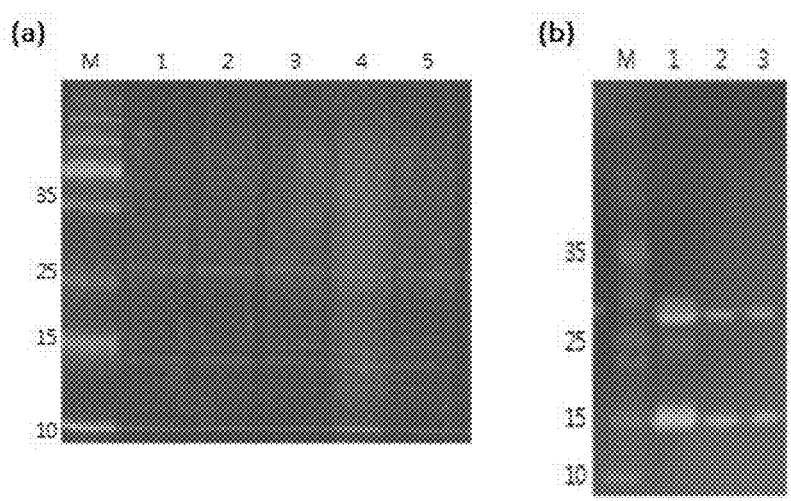
FIG. 5 shows the results of examining the expression and secretion of an HSA-IL2 fusion protein and interleukin-2 from *H. polymorpha* transformed with a pHSAft-1-IL-2 vector.

The results are shown in FIGS. 4 and 5.

As shown in FIG. 4, four samples were confirmed to have the HSA-IL2 fusion protein expressed and secreted from *H. polymorpha* (strain R4) transformed with the pHSAft-5-IL-2 vector. When the four samples were treated with ProTEV, it was shown that only a 13.4-kDa band was detected (#1 to #4). In addition, a protein expressed as a fusion protein with HSA was found at 47.3 kDa (#5 to #8).

As shown in FIG. 5, in the sample confirmed to have the HSA-IL2 fusion protein expressed and secreted from *H. polymorpha* (strain B8) transformed with the pHSAft-1-IL-2 vector, expression and secretion of a HSA-IL-2 fusion protein having a size of 28 kDa was observed (FIG. 5 (*a*)). When the fusion protein was treated with ProTEV, it was shown that interleukin-2 having a size of about 14 kDa was separated from the fusion protein (FIG. 5 (*b*)).

EXAMPLE 4

Optimization of Process for Producing Interleukin-2 Using Transformed Methylotrophic Yeast Using the *H. polymorpha* (B8) strain finally selected as an excellent strain for producing recombinant interleukin-2, experiments for optimizing culture conditions were performed. Specifically, using YP medium (2% (w/v) bacto-peptone, 1% (w/v) bacto-yeast extract) as a basal medium, experiments for determining optimal culture condition parameters, including methanol concentration, culture temperature, culture pH and shaking speed (rpm), were performed in a shaker [SI-300R, Lab Companion] at 1% seed volume.

In the experiments, the methanol concentration was changed from 2% (w/v), 3% (w/v), 4% (w/v) or 5% (w/v); the temperature was changed from 30° C., 35° C., 37° C. or 40° C.; the pH in seeding was changed from 5.5, 6.0, 6.5 or 7.0; and the shaking speed was changed from 150, 180, 200, 250 or 300 rpm. The final OD value and protein amount in the strain cultured for 30 hours under each of the conditions were measured according to the above-described methods.

4-1: Optimization of Methanol Concentration

A *H. polymorpha* strain is the yeast that contains a strong MOX promoter, and thus can easily assimilate methanol that is an inexpensive carbon source. Thus, the use of methanol as a fermentation substrate makes it possible to reduce the raw material cost and is very advantageous in terms of the production process, compared to the use of glucose.

In order to examine the effects of the initial methanol concentration on cell growth and protein production in *H. polymorpha*, the methanol concentration was changed from 2% (w/v) to 5% (w/v), and cell growth and protein production at each methanol concentration were measured. As a result, as can be seen in Table 5 below, cell growth and protein production in *H. polymorpha* were the highest at the initial methanol concentration of 3% (w/v).

TABLE 5

| Cell growth and protein production at varying methanol concentrations (*average values) | | |
|---|---|---|
| Methanol concentration (%) | Cell growth* (OD) | Total proteins* (µg/ml) |
| 2 | 3.48 | 2.10 |
| 3 | 3.98 | 2.16 |
| 4 | 3.85 | 2.13 |
| 5 | 2.96 | 2.12 |

4-2: Optimization of Culture Temperature

In order to examine the effects of the culture temperature on cell growth and protein production in *H. polymorpha*, the culture temperature was changed from 30, 35, 37 and 40° C., and cell growth and protein production at each culture temperature were measured. As a result, as can be seen in Table 6 below, cell growth and protein production in *H. polymorpha* were the highest at the culture temperature of 37° C.

TABLE 6

| Cell growth and protein production at varying culture temperatures (*average values) | | |
|---|---|---|
| Temperature (° C.) | Cell growth* (OD) | Total protein* (µg/ml) |
| 30 | 3.03 | 2.08 |
| 35 | 3.31 | 2.14 |
| 37 | 5.51 | 2.16 |
| 40 | 4.44 | 2.14 |

4-3: Optimization of Culture pH

In order to examine the effects of the culture pH on cell growth and protein production in *H. polymorpha*, the pH was changed from 5.5, 6.0. 6.5, and 7.0, and cell growth and protein production at each culture pH were measured. As a result, as can be seen in Table 7 below, cell growth and protein production in *H. polymorpha* were the highest at the culture pH of 6.0.

TABLE 7

Cell growth and protein production at varying culture pH (*average values)

| pH | Cell growth* (OD) | Total protein* (μg/ml) |
|---|---|---|
| 5.5 | 4.57 | 2.11 |
| 6.0 | 5.22 | 2.16 |
| 6.5 | 5.04 | 2.14 |
| 7.0 | 4.91 | 2.13 |

4-4: Optimization of Shaking Speed

In order to examine the effects of the shaking speed on cell growth and protein production in *H. polymorpha*, the shaking speed was changed from 150, 180, 200 and 250 rpm, and cell growth and protein production at each shaking speed were measured. As a result, as can be seen in Table 8 below, cell growth and protein production in *H. polymorpha* were the highest at the shaking speed of 200 rpm.

TABLE 8

Cell growth and protein production at varying shaking speeds (*average values)

| shaking speed (rpm) | Cell growth* (OD) | Total protein* (μg/ml) |
|---|---|---|
| 150 | 4.99 | 2.04 |
| 180 | 5.15 | 2.14 |
| 200 | 5.42 | 2.16 |
| 250 | 5.37 | 2.15 |

The above-described experiments for optimization indicated that the optimal culture conditions for producing interleukin-2 using *H. polymorpha* are the initial methanol concentration of 3% (w/v), the culture temperature of 37° C., the pH of 6.0, and the shaking speed of 200 rpm.

EXAMPLE 5

Production of Interleukin-2 Using Fermenter

The production of recombinant interleukin-2 was performed using a 5-liter fermenter under the following optimal culture conditions determined in the experiments for optimization: the initial methanol concentration of 3% (w/v), the culture temperature of 37° C., the pH of 6.0, and the shaking speed of 200 rpm.

The finally selected recombinant *H. polymorpha* strain seeded in YPD medium (2% (w/v) bacto-peptone, 1% (w/v) bacto-yeast extract, 2% (w/v) D-glucose) was seeded in YPM medium (2% (w/v) bacto-peptone, 1% (w/v) bacto-yeast extract, 3% (w/v) methanol). 200 ml of the medium containing the seeded strain was cultured in a shaker [SI-300R, Lab Companion] at 200 rpm for 30 hours at 37° C. and used as a seed culture. A 5-liter fermenter [KoBioTech, KF-5L, Korea] having a working volume of 3.5 liter was filled with YPM medium (2% (w/v) bacto-peptone, 1% (w/v) bacto-yeast extract, 3% (w/v) methanol). Using computer-aided automatic adjustment device, the culture pH was adjusted to 5.90-6.05 with 2N HCl and 2N NaCOH, and the culture temperature was adjusted to a range of 36.5° C. to 37.5° C., and the RT value was adjusted to 300. Under such conditions, the strain was cultured for a total of 30 hours while a sample was collected at 2-hour intervals. Using the sample, cell growth and protein production were measured according to the above-described methods.

Figure 6:
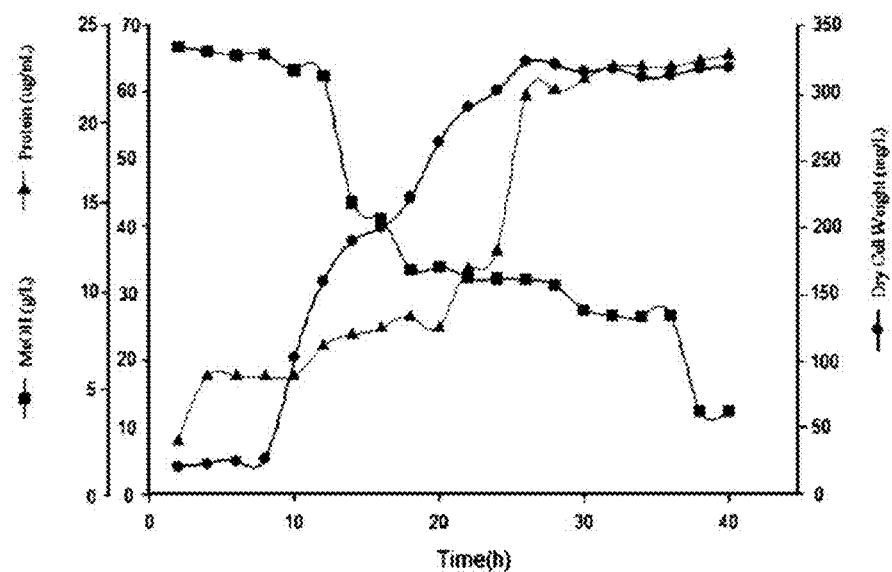
FIG. 6 shows the results of examining the changes in cell growth and protein expression as a function of time in a process of producing interleukin-2 by use of a fermenter.

The results of measuring cell growth and protein production are shown in FIG. 6.

As shown in FIG. 6, cell growth with an exponential growth phase occurred until 24 hours after seeding. However, after 24 hours, cell growth not longer occurred while the OD value decreased. Meanwhile, total protein production did not greatly increase until 10 hours of culture, but started to increase slightly after 10 hours of culture and started to increase rapidly after 15 hours of culture, and protein production was continued until 30 hours after the start of culture.

Furthermore, in order to examine whether the produced protein would be expressed as a fusion protein of HSA-IL-2 and would be efficiently secreted into the cell culture medium, the cell culture medium was centrifuged in the same manner as described in Example 3 to remove the cells. The supernatant, which the cells were removed, was concentrated with TCA, and then subjected to SDS-PAGE to separate protein. Based on the band size of the separated protein, the presence of the fusion protein was confirmed. The results are shown in FIGS. 7 and 8.

Figure 7:
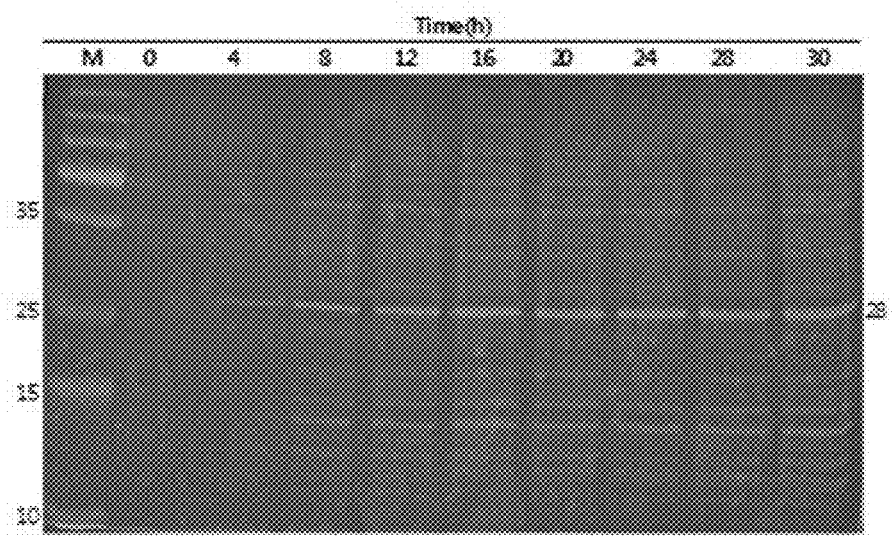
FIG. 7 shows the results of examining the change in expression level of a human serum albumin/interleukin-2 fusion protein as a function of time.

As can be seen in FIG. 7, the expression level of an about 28 kDa protein increased gradually with the passage of culture time. In addition, it could be seen that, after about 15 hours, the fusion protein was overexpressed while the band of the protein became clearer.

Figure 8:
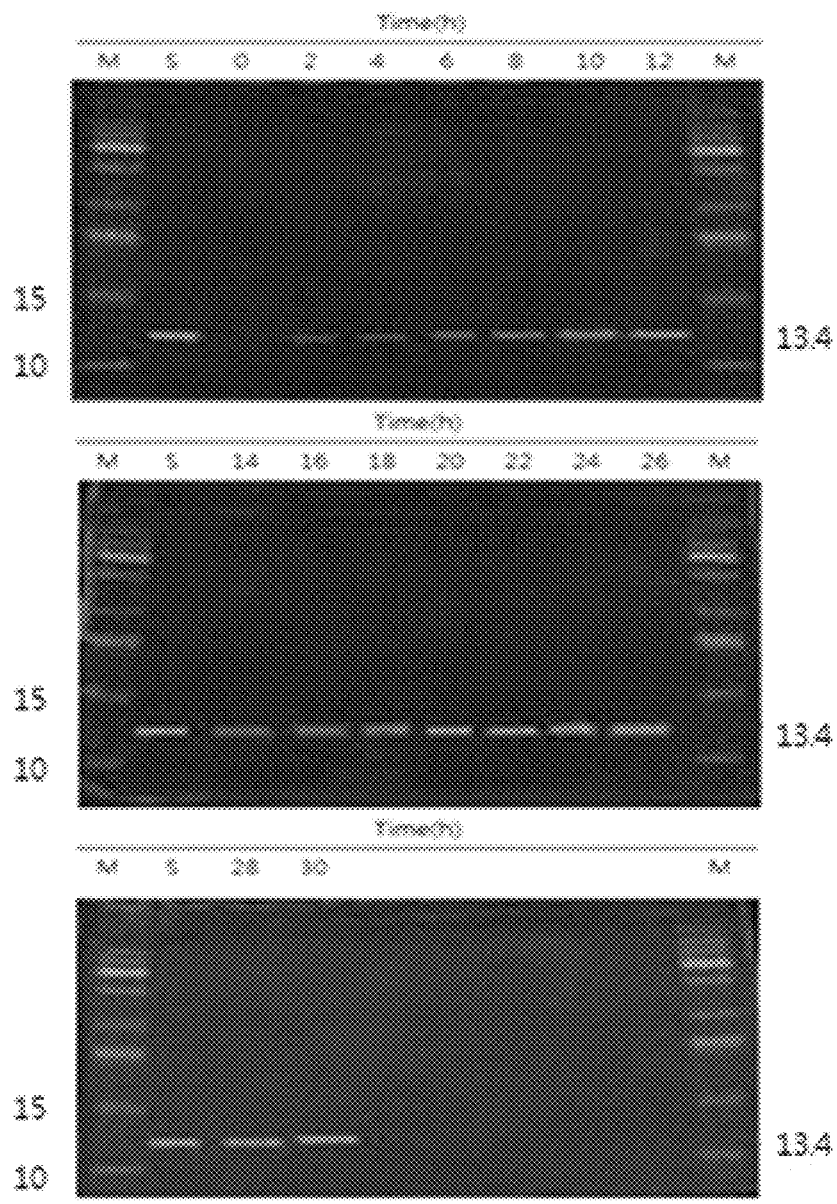
FIG. 8 shows the results of examining the change in expression level of interleukin-2 in a TEV protease-treated culture supernatant as a function of time.

As can be seen in FIG. 8, in the case of the protein samples treated with ProTEV Plus at varying time points during culture, a 14-kDa protein band was detected and became clearer with the passage of culture time.

Figure 9:
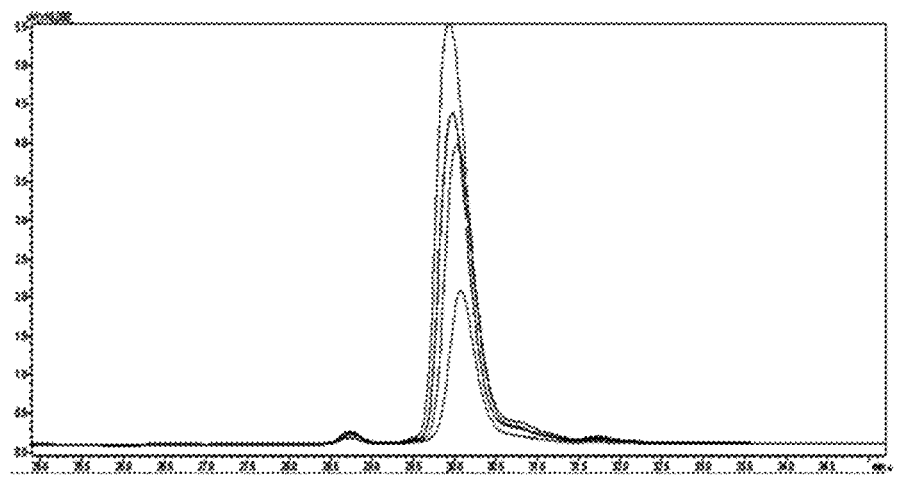
FIG. 9 shows the results of analyzing the time-dependent production of interleukin-2 by HPLC.

In addition, the protein solution was treated with ProTEV Plus in order to examine whether or not recombinant interleukin-2 would be separated from the fusion protein. The treated protein was further analyzed by HPLC. For HPLC analysis, purified samples were filtered using a 0.45 μl syringe filter and a syringe, and then loaded onto HPLC [SIMADZU, Prominence, Japan]. Vision HT C18 HL column (5μ, length 250 nm) was used as the HPLC column, and samples were measured for 60 minutes at a flow rate of 1.0 ml/min, a temperature of 30° C., a wavelength of 280 nm and in a ratio range of 10. The results of the HPLC analysis are shown in FIG. 9. In FIG. 9, the green color indicates standard interferon-2; the brown color indicates the sample after 16 hours; the black color indicates the sample after 20 hours; and the blue color indicates the sample after 30 hours As can be seen in FIG. 9, the peak of recombinant interleukin-2 appeared at the same time as that of standard interleukin-2 and the width of the peak increased with the passage of time, a large amount of recombinant interleukin-2 was produced.

EXAMPLE 6

Fermentation Kinetics of Transformed Methylotrophic Yeast

Fermentation kinetics in the production of recombinant interleukin-2, performed using *H. polymorpha*, were measured, and the results are shown in Table 9 below.

As shown in Table 9 below, the following results were obtained: a cell growth rate of 10 mg/l/hr, a methanol (MeOH) consumption rate of 0.67 g/l/hr, a protein production rate of 2.17 mg/l/hr, a cell growth yield of 15 mg/g, a protein production yield of 3.25 µg/g, and a protein productivity of 1.1 µg/g/hr.

TABLE 9

Fermentation kinetics of transformed methylotrophic yeast

| Kinetic parameters | Values |
| --- | --- |
| Cell growth rate (mg/l/hr) | 10 |
| MeOH consumption rate (g/l/hr) | 0.67 |
| Protein production rate (mg/l/hr) | 2.17 |

TABLE 9-continued

Fermentation kinetics of transformed methylotrophic yeast

| Kinetic parameters | Values |
| --- | --- |
| Cell growth yield (mg/g) | 15 |
| Protein yield (µg/g) | 3.25 |
| Protein productivity (µg/g/hr) | 1.1 |

Depository Authority: Korean Research Institute of Bioscience and Biotechnology;
Accession Number: KCTC 18329P;
Date of Deposition: Oct. 1, 2014.
Converted on Dec. 14, 2018 to a deposit under the Budapest Treaty at the Korean Collection for Type Cultures as accession number KCTC 13777BP.

The invention claimed is:

1. A method for producing interleukin-2, comprising:

(a) cloning an interleukin-2 expression construct for yeast, wherein the expression construct comprises a methanol oxidase (MOX) promoter, a human serum albumin gene fragment having a nucleotide sequence of SEQ ID NO:3, and an interleukin-2 gene;

(b) transforming yeast host cells with the expression construct prepared in (a), and culturing the transformed yeast cells to express interleukin-2; and (c) isolating the expressed interleukin-2 from the transformed yeast cells cultured in (b).

2. The method of claim 1, wherein the expression construct in (a) further comprises a tobacco etch virus protease site.

3. The method of claim 1, wherein the yeast host cells in (b) is any one selected from among *Hansenula polymorpha, Pichia pastoris, Candia boidini, Pichia methanolica,* and *Ogataea minuta*.

4. The method of claim 1, wherein the culturing in (b) is performed in YPM medium.

5. The method of claim 4, wherein the culturing in (b) is performed under the following conditions: a methanol concentration of 1% (w/v) to 10% (w/v), a culture temperature of 25° C. to 45° C., a culture pH of 4.5 to 7.0, and a shaking speed of 100 to 300 rpm.

6. The method of claim 1, wherein the methanol oxidase (MOX) promoter has a nucleotide sequence of SEQ ID NO:1 and the interleukin-2 gene has a nucleotide sequence of SEQ ID NO:4.

7. A method for producing interleukin-2, comprising:
(a) culturing *Hansenula polymorpha* transformed with an interleukin-2 expression construct for yeast,
wherein the expression construct comprises a methanol oxidase (MOX) promoter, a human serum albumin (HSA) gene fragment having a nucleotide sequence of SEQ ID NO:3, a tobacco etch virus protease site, and an interleukin-2 (IL-2) gene, and produces a HSA-IL-2 fusion protein comprising HSA, IL-2, and a tobacco etch virus protease cleavage site;
(b) isolating the HSA-IL-2 fusion protein from the culture of (a); and
(c) treating the isolated protein of (b) with tobacco etch virus protease to separate the interleukin-2.

8. The method of claim 7, wherein the transformed *Hansenula polymorpha* in (a) is a strain deposited under accession number *Hansenula polymorpha* KCTC 13777BP.

9. The method of claim 7, wherein the culturing in (a) is performed in YPM medium.

10. The method of claim 9, wherein the culturing in (a) is performed under the following conditions: a methanol concentration of 1% (w/v) to 10% (w/v), a culture temperature of 25° C. to 45° C., a culture pH of 4.5 to 7.0, and a shaking speed of 100 to 300 rpm.

11. The method of claim 7, wherein the treating with the tobacco etch virus protease is performed at a temperature of 28° C. to 32° C. for 4 to 8 hours.

* * * * *

SEQUENCE LISTING

```
<160> NUMBER OF SEQ ID NOS: 15

<210> SEQ ID NO 1
<211> LENGTH: 1523
<212> TYPE: DNA
<213> ORGANISM: Hansenula polymorpha
<220> FEATURE:
<221> NAME/KEY: promoter
<222> LOCATION: (1)..(1523)
<223> OTHER INFORMATION: MOX promoter

<400> SEQUENCE: 1
gcgaagaacg atctcctcga gctgttcgcg gatcagcttg tagccctgca gtggaaccag      60
gccgacggcc cgctccttgc ggaccacggt ggctggcgcg cccaatttgt gaaccaggtc     120
gtttaggacc tcctgcgcaa agtccagtgt taggagaatg tcctcctggg accaattcag     180
catgttctcg agcagccatc tgtctttgga gtaaaaacgt aatttctgct cctcgttact     240
gtaccggaaa agataatttg cctcgccgcc cataataaga aggttctttt tctggtggcc     300
tttgagcagc ggggacgttt ggacagcgtc gatgaggccc ttgaggcgct cgtagtactt     360
ggtcgcgtcg ttgtagccgg ccgcggtgac gatacccaca taaaggtctt tggccattag     420
cttgatgagg tggggtaaga tgggcgactc ggcatcgaaa tttttgccgt cgtcgtacag     480
tgtgatgtca ccatcgaatg ttatgagctg cagcttgcga tctcggatgg ttttggaatg     540
gaagaaccgc gacatctcca acagctgggc cgtgttgagg atgagccgga cgtcgttgaa     600
cgagggcgcc acaagccggc gtttgctgat ggcgcggcgc tcgtcctcga tgtagaaggc     660
cttttccaga ggcagtctgg tgaaaaagtt gccaacgctc ggaaccagct gcacgagccg     720
agacaattcg ggggtgccgg cttttggtcat ttcaatgttg tcgtcgatga ggagttcgag     780
gtcgtggaag atttctgcgt aacggcgttt tgcctcagag ttcaccatga gatcgtccac     840
ggcggagatg ccgttgctct tcaccgcgta caggacgaac ggcgtggcca acaggccctt     900
tatccactct atgaggccgt ctcgacggtg ttccttgagt gcatactcca ctctgtagcg     960
actagtcatc cggaggctgg gctttctgcg ctgggtgtac taattaattg gtgccgcacc    1020
tgtacggggt accttgcatc cttgcaccgc aactaaaata aacccactcg ctttagcctt    1080
cgcgtaaaac tcgtgaatct ggcaactgag ggggttctgc agccgcaacc aaactttatc    1140
gctttgagga cgcagctgga tggtgtcatg tgaggctctg ttctctggcg tagcctacaa    1200
cgtgactttg cctaagcgga cggccctacc cttagctgcc tgcgcctgct accagaaaat    1260
cactagaaca gcagagggcc gatgtggtaa ttggtgcggt gtcggccagt ctgtttctcc    1320
acagtgcaaa tgcgggtgaa ccggccagaa agcaaatttc ttatgctacc gtgcagtgac    1380
```

| | |
|---|---|
| tccgacatcc ccagttttg ccctacttga tcacagatgg ggtcagcact gtcgctaagt | 1440 |
| gcacccagtc gtccccacac gcgcaatcta taaatactgc cgccagtgca cggtggtgac | 1500 |
| atcaatctaa agtacaaaaa caa | 1523 |

<210> SEQ ID NO 2
<211> LENGTH: 1824
<212> TYPE: DNA
<213> ORGANISM: Homo sapiens
<220> FEATURE:
<221> NAME/KEY: gene
<222> LOCATION: (1)..(1824)
<223> OTHER INFORMATION: Human serum albumin

<400> SEQUENCE: 2

| | |
|---|---|
| atgaagtggg taacctttat ttccttctt tttctcttta gctcggctta ttccagggt | 60 |
| gtgtttcgtc gagatgcaca caagagtgag gttgctcatc ggtttaaaga tttgggagaa | 120 |
| gaaaatttca aagccttggt gttgattgcc tttgctcagt atcttcagca gtgtccattt | 180 |
| gaagatcatg taaaattagt gaatgaagta actgaatttg caaaaacatg tgttgctgat | 240 |
| gagtcagctg aaaattgtga caaatcactt catacccttt ttggagacaa attatgcaca | 300 |
| gttgcaactc ttcgtgaaac ctatggtgaa atggctgact gctgtgcaaa acaagaacct | 360 |
| gagagaaatg aatgcttctt gcaacacaaa gatgacaatc caaatctccc ccgattggtg | 420 |
| agaccagagg ttgatgtgat gtgcactgct tttcatgaca tgaagagac attttgaaa | 480 |
| aaatacttat atgaaattgc cagaagacat ccttactttt atgccccgga actccttttc | 540 |
| tttgctaaaa ggtataaagc tgcttttaca gaatgttgcc aagctgctga taaagcagcc | 600 |
| tgcctgttgc caaagctcga tgaacttcgg gatgaaggga aggcttcgtc tgccaaacag | 660 |
| agactcaagt gtgccagtct ccaaaaattt ggagaaagag ctttcaaagc atgggcagta | 720 |
| gctcgcctga ccagagatt tcccaaagct gagtttgcag aagtttccaa gttagtgaca | 780 |
| gatcttacca aagtccacac ggaatgctgc catggagatc tgcttgaatg tgctgatgac | 840 |
| agggcggacc ttgccaagta tatctgtgaa aatcaagatt cgatctccag taaactgaag | 900 |
| gaatgctgtg aaaaacctct gttggaaaaa tcccactgca ttgccgaagt ggaaaatgat | 960 |
| gagatgcctg ctgacttgcc ttcattagcg gctgattttg ttgaaagtaa ggatgtttgc | 1020 |
| aaaaactatg ctgaggcaaa ggatgtcttc ttgggcatgt ttttgtatga atatgcaaga | 1080 |
| aggcatcctg attactctgt cgtactgctg ctgagacttg ccaagacata tgaaaccact | 1140 |
| ctagagaagt gctgtgccgc tgcagatcct catgaatgct atgccaaagt gttcgatgaa | 1200 |
| tttaaacctc ttgtggaaga gcctcagaat ttaatcaaac aaaattgtga gcttttgag | 1260 |
| cagcttggag agtacaaatt ccagaatgcg ctattagttc gttacaccaa gaaagtaccc | 1320 |
| caagtgtcaa ctccaactct tgtagaggtc tcaagaaacc taggaaaagt gggcagcaaa | 1380 |
| tgttgtaatc ctgaagcaaa aagaatgcc tgtgcagaag actatctatc cgtggtcctg | 1440 |
| aaccagttat gtgtgttgca tgagaaaacg ccagtaagtg acagagtcac caaatgctgc | 1500 |
| acagaatcct tggtgaacag gcgaccatgc ttttcagctc tggaagtcga tgaaacatac | 1560 |
| gttcccaaag agtttaatgc tgaaacattc accttccatg cagatatatg cacactttct | 1620 |
| gagaaggaga gacaaatcaa gaaacaaact gcacttgttg agcttgtgaa acacaagccc | 1680 |
| aaggcaacaa aagagcaact gaaagctgtt atggatgatt tcgcagcttt tgtagagaag | 1740 |
| tgctgcaagg ctgacgataa ggaaacctgc tttgccgagg agggtaaaaa acttgttgct | 1800 |

<210> SEQ ID NO 3
<211> LENGTH: 411
<212> TYPE: DNA
<213> ORGANISM: Homo sapiens
<220> FEATURE:
<221> NAME/KEY: gene
<222> LOCATION: (1)..(411)
<223> OTHER INFORMATION: fragment of human serum albumin

<400> SEQUENCE: 3

```
atgaagtggg taacctttat ttccttctt tttctcttta gctcggctta ttccaggggt      60
gtgtttcgtc gagatgcaca caagagtgag gttgctcatc ggtttaaaga tttgggagaa     120
gaaaatttca agccttggt gttgattgcc tttgctcagt atcttcagca gtgtccattt     180
gaagatcatg taaaattagt gaatgaagta actgaatttg caaaaacatg tgttgctgat    240
gagtcagctg aaaattgtga caaatcactt catacccttt ttggagacaa attatgcaca    300
gttgcaactc ttcgtgaaac ctatggtgaa atggctgact gctgtgcaaa acaagaacct    360
gagagaaatg aatgcttctt gcaacacaaa gatgacaatc caaatctccc c             411
```

<210> SEQ ID NO 4
<211> LENGTH: 399
<212> TYPE: DNA
<213> ORGANISM: Homo sapiens
<220> FEATURE:
<221> NAME/KEY: gene
<222> LOCATION: (1)..(399)
<223> OTHER INFORMATION: Interleukin-2

<400> SEQUENCE: 4

```
atgcctactt caagttctac aaagaaaaca cagctacaac tggaacattt actgctggat      60
ttacagatga ttttgaatgg aattaataat tacaagaatc ccaaactcac caggatgctc    120
acatttaagt tttacatgcc caagaaggcc acagaattga acatcttca gtgtctagaa     180
gaagaactca aacctctgga ggaagtgcta aatttagctc aaagcaaaaa ctttcactta    240
agacccaggg acttaatcag caatatcaac gtaatagttc tggaactaaa gggatctgaa    300
acaacattca tgtgtgaata tgctgatgag acagcaacca ttgtagaatt tctgaacaga    360
tggattacct tttctcagag catcatctca acactgact                            399
```

<210> SEQ ID NO 5
<211> LENGTH: 21
<212> TYPE: DNA
<213> ORGANISM: Artificial Sequence
<220> FEATURE:
<223> OTHER INFORMATION: Tobacco etch virus site

<400> SEQUENCE: 5

```
gaaaacctgt attttcaggg c                                                21
```

<210> SEQ ID NO 6
<211> LENGTH: 10167
<212> TYPE: DNA
<213> ORGANISM: Artificial Sequence
<220> FEATURE:
<223> OTHER INFORMATION: pHSAft-5-IL-2 sequence
<220> FEATURE:
<221> NAME/KEY: gene
<222> LOCATION: (7370)..(9193)
<223> OTHER INFORMATION: Human serum Albumin
<220> FEATURE:
<221> NAME/KEY: gene

```
<222> LOCATION: (9200)..(9223)
<223> OTHER INFORMATION: His tag
<220> FEATURE:
<221> NAME/KEY: gene
<222> LOCATION: (9224)..(9253)
<223> OTHER INFORMATION: linker
<220> FEATURE:
<221> NAME/KEY: gene
<222> LOCATION: (9254)..(9274)
<223> OTHER INFORMATION: TEV site
<220> FEATURE:
<221> NAME/KEY: gene
<222> LOCATION: (9281)..(9679)
<223> OTHER INFORMATION: Interleukin-2
<220> FEATURE:
<221> NAME/KEY: gene
<222> LOCATION: (9686)..(9709)
<223> OTHER INFORMATION: Strep-tag

<400> SEQUENCE: 6
gcttatcggg ccgctctagg atcctacttt tttttctccc ttatttagtt cttgagtagc      60
ttggccacct cctgcgcaac agcatcacca acttcctgtg ttgaggagct tccacccaaa     120
tcggcagtca tgatacctgc atccaggacg ttcttgacgg cctgctcgat cgcacggccg     180
gcatccacca agtccagcga cagcttcagc atcatggcgg cagacaaaat tgtggccaat     240
ggattgacct tgcccgggcc caaatctggc gccgagccgt ggcagggctc gtaaagacca     300
aacgccttgt ttgtgtctgg cagagacgcc aacgaggcag aaggcagcag gcccagagac     360
ccaggaatca cactggcctc gtcactgatg atgtcgccaa acatgttgtt ggtgacaatg     420
acaccgttga gtttcgttgg cgacttgacc aaaatcatgg ctgccgagtc gatcagctgg     480
tgctgcaccg tcagctgcgg gaactcgttc ttgatggtct cctcaacagt cttccgccac     540
aaacgcgagg atgcaagcac gttggctttg tccagcgacc acagtgggag cggtgggtcg     600
ctctgcagcg ccaaaaaggc cgccattctc gtgattctct gcacctctgg aacagaatag     660
ctctcagtgt cgctggcaac tccgtcgccg gcatcctcct tgcggtcacc aaagtagatt     720
ccaccaacca actcacgcac aacaacaaag tcagtgccct tgacgatttc tgatttcagt     780
ggagatagct tcagaagagc gtcggaagca aaactgcatg gacgcaggtt cgcgtacaag     840
ttgagctctt ttctgatctt caacagaccc tgctcaggac gcacggagcc ggttccccac     900
ttaggtcctc cgacggctcc aagcaaaacg gcgtcagcct tcttggcggc ttcgagggcc     960
tcgtcggaca atggcacccc ataagcatcg atcgaggcac cgccgatcag gtgcttggaa    1020
aagttgaact taacgccgat tgccgacgag acagcctcga aaccttgac ggcctccgca    1080
acaacctcgg ggcccacgtg atcaccaggg agaagcacaa tgttcttact catgattgca    1140
aaatgatgca actatttttgc gccggtaccg ggaaaaattg aaaaaccatc cacttactca    1200
ttcctgtctt tttatttcgt attaccaaac cgcttacgta ctcacccact cagatccccc    1260
gggctgcagg aattggatcc gaccagtctc tctcgcacat tatcaattgc tctttagtac    1320
aaagataata tagaaacaat attcgaatta attcgttatg agccatattc aacgggaaac    1380
gtcttgctcg aggccgcgat taaattccaa catggatgct gatttatatg ggtataaatg    1440
ggctcgcgat aatgtcgggc aatcaggtgc gacaatctat cgattgtatg ggaagcccga    1500
tgcgccagag ttgtttctga acatggcaa aggtagcgtt gccaatgatg ttacagatga    1560
gatggtcaga ctaaactggc tgacggaatt tatgcctctt ccgaccatca agcattttat    1620
ccgtactcct gatgatgcat ggttactcac cactgcgatc cccgggaaaa cagcattcca    1680
ggtattagaa gaatatcctg attcaggtga aaatattgtt gatgcgctgg cagtgttcct    1740
```

```
gcgccggttg cattcgattc ctgtttgtaa ttgtccttt  aacagcgatc gcgtatttcg    1800
tctcgctcag gcgcaatcac gaatgaataa cggtttggtt gatgcgagtg attttgatga    1860
cgagcgtaat ggctggcctg ttgaacaagt ctggaaagaa atgcataagc ttttgccatt    1920
ctcaccggat tcagtcgtca ctcatggtga tttctcactt gataacctta ttttttgacga   1980
ggggaaatta ataggttgta ttgatgttgg acgagtcgga atcgcagacc gataccagga    2040
tcttgccatc ctatggaact gcctcggtga gttttctcct tcattacaga aacggctttt    2100
tcaaaaatat ggtattgata atcctgatat gaataaattg cagtttcatt tgatgctcga    2160
tgagtttttc taatcagaat tggttaattg gttgtaacac tggcagagca ttacgctgac    2220
ttgacgggac ggcggctttg ttgaataaat cgaacttttg ctgagttgaa ggatcagatc    2280
acgcatcttc ccgacaacgc agaccgttcc gtggcaaagc aaaagttcaa atcaccaac     2340
tggtccacct acaacaaagc tctcatcaac cgtggctccc tcactttctg gctggatgat    2400
ggggcgattc aggcctggta tgagtcagca acaccttctt cacgaggcag acctcagcgc    2460
cccccccct gcagtcgaca ggccaacgtg ttgtgcgg agtcggtggt gtttagagag       2520
gaattagagc aagtagaagt atagaaggaa taagccaagt agagacaagt ttaatatatg    2580
tagattaata aaggtgagga attagatggg gaggaagcgg caggaagcgg tgtagggatg    2640
cggcgaggaa agcagaggca gctggtttca ggacgcggtc tgaggcctgg ggtggcgggg    2700
tggcggggtg gcggggtggc ggggtggcgg ggtggcgggg tggcggggtg gcggggtggc    2760
ggggtggcgg ggtggcgggg tggcggggtg gcggggtggc ggggtggcgg ggtggcgggg    2820
tggcggggtg gcggggtggc ggggtggcgg ggtggcgggg tggcggggtg gcgatcaagc    2880
ttatcgatac cgtcgacctc gagggggggc ccggtaccca gcttttgttc cctttagtga    2940
gggttaattg cgcgcttggc gtaatcatgg tcatagctgt ttcctgtgtg aaattgttat    3000
ccgctcacaa ttccacacaa catacgagcc ggaagcataa agtgtaaagc ctggggtgcc    3060
taatgagtga gctaactcac attaattgcg ttgcgctcac tgcccgcttt ccagtcggga    3120
aacctgtcgt gccagctgca ttaatgaatc ggccaacgcg cggggagagg cggtttgcgt    3180
attgggcgct cttccgcttc ctcgctcact gactcgctgc gctcggtcgt tcggctgcgg    3240
cgagcggtat cagctcactc aaaggcggta atacggttat ccacagaatc aggggataac    3300
gcaggaaaga acatgtgagc aaaaggccag caaaaggcca ggaaccgtaa aaaggccgcg    3360
ttgctggcgt ttttccatag gctccgcccc cctgacgagc atcacaaaaa tcgacgctca    3420
agtcagaggt ggcgaaaccc gacaggacta taaagatacc aggcgtttcc ccctggaagc    3480
tccctcgtgc gctctcctgt tccgaccctg ccgcttaccg gatacctgtc cgcctttctc    3540
ccttcgggaa gcgtggcgct ttctcatagc tcacgctgta ggtatctcag ttcggtgtag    3600
gtcgttcgct ccaagctggg ctgtgtgcac gaaccccccg ttcagcccga ccgctgcgcc    3660
ttatccggta actatcgtct tgagtccaac ccggtaagac acgacttatc gccactggca    3720
gcagccactg gtaacaggat tagcagagcg aggtatgtag cggtgctac  agagttcttg    3780
aagtggtggc ctaactacgg ctacactaga aggacagtat ttggtatctg cgctctgctg    3840
aagccagtta ccttcggaaa aagagttggt agctcttgat ccggcaaaca aaccaccgct    3900
ggtagcggtg gtttttttgt ttgcaagcag cagattacgc gcagaaaaaa aggatctcaa    3960
gaagatcctt tgatctttc  tacgggtct gacgctcagt ggaacgaaaa ctcacgttaa    4020
gggattttgg tcatgagatt atcaaaaagg atcttcacct agatcctttt aaattaaaaa    4080
tgaagtttta aatcaatcta agtatatat  gagtaaactt ggtctgacag ttaccaatgc    4140
```

```
ttaatcagtg aggcacctat ctcagcgatc tgtctatttc gttcatccat agttgcctga    4200
ctccccgtcg tgtagataac tacgatacgg gagggcttac catctggccc cagtgctgca    4260
atgataccgc gagacccacg ctcaccggct ccagatttat cagcaataaa ccagccagcc    4320
ggaagggcca agcgcagaag tggtcctgca actttatccg cctccatcca gtctattaat    4380
tgttgccggg aagctagagt aagtagttcg ccagttaata gtttgcgcaa cgttgttgcc    4440
attgctacag gcatcgtggt gtcacgctcg tcgtttggta tggcttcatt cagctccggt    4500
tcccaacgat caaggcgagt tacatgatcc cccatgttgt gcaaaaaagc ggttagctcc    4560
ttcggtcctc cgatcgttgt cagaagtaag ttggccgcag tgttatcact catggttatg    4620
gcagcactgc ataattctct tactgtcatg ccatccgtaa gatgcttttc tgtgactggt    4680
gagtactcaa ccaagtcatt ctgagaatag tgtatgcggc gaccgagttg ctcttgcccg    4740
gcgtcaatac gggataatac cgcgccacat agcagaactt taaaagtgct catcattgga    4800
aaacgttctt cggggcgaaa actctcaagg atcttaccgc tgttgagatc cagttcgatg    4860
taacccactc gtgcacccaa ctgatcttca gcatctttta ctttcaccag cgtttctggg    4920
tgagcaaaaa caggaaggca aaatgccgca aaaaagggaa taagggcgac acggaaatgt    4980
tgaatactca tactcttcct ttttcaatat tattgaagca tttatcaggg ttattgtctc    5040
atgagcggat acatatttga atgtatttag aaaaataaac aaataggggt tccgcgcaca    5100
tttccccgaa aagtgccacc taaattgtaa gcgttaatat tttgttaaaa ttcgcgttaa    5160
attttttgtta aatcagctca ttttttaacc aataggccga atcggcaaa atcccttata    5220
aatcaaaaga atagaccgag atagggttga gtgttgttcc agtttggaac aagagtccac    5280
tattaaagaa cgtggactcc aacgtcaaag ggcgaaaaac cgtctatcag ggcgatggcc    5340
cactacgtga accatcaccc taatcaagtt ttttggggtc gaggtgccgt aaagcactaa    5400
atcggaaccc taaagggagc ccccgattta gagcttgacg ggaaagccg gcgaacgtgg    5460
cgagaaagga agggaagaaa gcgaaaggag cgggcgctag gcgctggca agtgtagcgg    5520
tcacgctgcg cgtaaccacc acacccgccg cgcttaatgc gccgctacag gcgcgtccc    5580
attcgccatt caggctgcgc aactgttggg aagggcgatc ggtgcgggcc tcttcgctat    5640
tacgccagct ggcgaaaggg ggatgtgctg caaggcgatt aagttgggta acgccagggt    5700
tttcccagtc acgacgttgt aaaacgacgg ccagtgagcg cgcgtaatac gactcactat    5760
agggcgaatt ggagctccac cgcggtggcg gccgtcgatc gacgcgaaga acgatctcct    5820
cgagctgttc gcggatcagc ttgtagccct gcagtggaac caggccgacg gcccgctcct    5880
tgcggaccac ggtggctggc gcgcccaatt tgtgaaccag gtcgtttagg acctcctgcg    5940
caaagtccag tgttaggaga atgtcctcct gggaccaatt cagcatgttc tcgagcagcc    6000
atctgtcttt ggagtaaaaa cgtaatttct gctcctcgtt actgtaccgg aaaagataat    6060
ttgcctcgcc gcccataata agaaggttct ttttctggtg gcctttgagc agcggggacg    6120
tttggacagc gtcgatgagg cccttgaggc gctcgtagta cttggtcgcg tcgttgtagc    6180
cggccgcggt gacgataccc acataaaggt ctttggccat tagcttgatg aggtggggta    6240
agatgggcga ctcggcatcg aaattttttgc cgtcgtcgta cagtgtgatg tcaccatcga    6300
atgttatgag ctgcagcttg cgatctcgga tggttttgga atggaagaac cgcgacatct    6360
ccaacagctg ggccgtgttg aggatgagcc ggacgtcgtt gaacgagggc gccacaagcc    6420
ggcgtttgct gatggcgcgg cgctcgtcct cgatgtagaa ggccttttcc agaggcagtc    6480
```

```
tggtgaaaaa gttgccaacg ctcggaacca gctgcacgag ccgagacaat tcggggtgc    6540 cggctttggt catttcaatg ttgtcgtcga tgaggagttc gaggtcgtgg aagatttctg   6600
cgtaacggcg ttttgcctca gagttcacca tgagatcgtc cacggcggag atgccgttgc   6660
tcttcaccgc gtacaggacg aacggcgtgg ccaacaggcc ctttatccac tctatgaggc   6720
cgtctcgacg gtgttccttg agtgcatact ccactctgta gcgactagtc atccggaggc   6780
tgggctttct gcgctgggtg tactaattaa ttggtgccgc acctgtacgg ggtaccttgc   6840
atccttgcac cgcaactaaa ataaacccac tcgctttagc cttgcgtaa aactcgtgaa    6900 tctggcaact gaggggggttc tgcagccgca accaaacttt atcgctttga ggacgcagct   6960
ggatggtgtc atgtgaggct ctgttctctg gcgtagccta caacgtgact ttgcctaagc   7020
ggacggccct accctttagct gcctgcgcct gctaccagaa aatcactaga acagcagagg   7080
gccgatgtgg taattggtgc ggtgtcggcc agtctgtttc tccacagtgc aaatgcgggt   7140
gaaccggcca gaaagcaaat tcttatgct accgtgcagt gactccgaca tcccccagttt   7200 ttgccctact tgatcacaga tggggtcagc actgtcgcta agtgcaccca gtcgtcccca   7260
cacgcgcaat ctataaatac tgccgccagt gcacggtggt gacatcaatc taaagtacaa   7320
aaacaaaagc ttgaattcgg cacgaggtca acccacgcc tttggcacaa tgaagtgggt    7380
aacctttatt tccctttcttt ttctctttag ctcggcttat tccaggggtg tgtttcgtcg   7440
agatgcacac aagagtgagg ttgctcatcg gtttaaagat tggggagaag aaaatttcaa   7500
agccttggtg ttgattgcct ttgctcagta tcttcagcag tgtccatttg aagatcatgt   7560
aaaattagtg aatgaagtaa ctgaatttgc aaaaacatgt gttgctgatg agtcagctga   7620
aaattgtgac aaatcacttc atacccttt tggagacaaa ttatgcacag ttgcaactct    7680
tcgtgaaacc tatggtgaaa tggctgactg ctgtgcaaaa caagaacctg agagaaatga   7740
atgcttcttg caacacaaag atgacaatcc aaatctcccc cgattggtga ccagaggt     7800 tgatgtgatg tgcactgctt ttcatgacaa tgaagagaca ttttgaaaa aatacttata    7860 tgaaattgcc agaagacatc cttacttta tgccccggaa ctccttttct ttgctaaaag    7920
gtataaagct gcttttacag aatgttgcca agctgctgat aaagcagcct gcctgttgcc   7980
aaagctcgat gaacttcggg atgaagggaa ggcttcgtct gccaaacaga gactcaagtg   8040
tgccagtctc caaaaatttg gagaaagagc tttcaaagca tgggcagtag ctcgcctgag   8100
ccagagattt cccaaagctg agtttgcaga agtttccaag ttagtgacag atcttaccaa    8160
agtccacacg gaatgctgcc atggagatct gcttgaatgt gctgatgaca gggcggacct   8220
tgccaagtat atctgtgaaa atcaagattc gatctccagt aaactgaagg aatgctgtga   8280
aaaacctctg ttggaaaaat cccactgcat tgccgaagtg gaaaatgatg agatgcctgc   8340
tgacttgcct tcattagcgg ctgattttgt tgaaagtaag gatgtttgca aaaactatgc   8400
tgaggcaaag gatgtcttct tgggcatgtt tttgtatgaa tatgcaagaa ggcatcctga   8460
ttactctgtc gtactgctgc tgagacttgc caagacatat gaaaccactc tagagaagtg   8520
ctgtgccgct gcagatcctc atgaatgcta tgccaaagtg ttcgatgaat ttaaacctct   8580
tgtggaagag cctcagaatt taatcaaaca aaattgtgag cttttttgagc agcttggaga   8640 gtacaaattc cagaatgcgc tattagttcg ttacaccaag aaagtacccc aagtgtcaac   8700
tccaactctt gtagaggtct caagaaacct aggaaaagtg ggcagcaaat gttgtaatcc   8760
tgaagcaaaa agaatgccct gtgcagaaga ctatctatcc gtggtcctga accagttatg   8820
tgtgttgcat gagaaaacgc cagtaagtga cagagtcacc aaatgctgca cagaatcctt   8880
```

```
ggtgaacagg cgaccatgct tttcagctct ggaagtcgat gaaacatacg ttcccaaaga    8940
gtttaatgct gaaacattca ccttccatgc agatatatgc acactttctg agaaggagag    9000
acaaatcaag aaacaaactg cacttgttga gcttgtgaaa cacaagccca aggcaacaaa    9060
agagcaactg aaagctgtta tggatgattt cgcagctttt gtagagaagt gctgcaaggc    9120
tgacgataag gaaacctgct ttgccgagga gggtaaaaaa cttgttgctg caagtcaagc    9180
tgccttaggc ttagttaacc atcaccatca ccatcaccat cacggtggcg gtggctcggg    9240
tggcggtgga tccgaaaacc tgtattttca gggcgctagc atgcctactt caagttctac    9300
aaagaaaaca cagctacaac tggaacattt actgctggat ttacagatga ttttgaatgg    9360
aattaataat tacaagaatc ccaaactcac caggatgctc acatttaagt tttacatgcc    9420
caagaaggcc acagaattga aacatcttca gtgtctagaa gaagaactca aacctctgga    9480
ggaagtgcta aatttagctc aaagcaaaaa ctttcactta gacccagggg acttaatcag    9540
caatatcaac gtaatagttc tggaactaaa gggatctgaa acaacattca tgtgtgaata    9600
tgctgatgag acagcaacca ttgtagaatt tctgaacaga tggattaccc tttctcagag    9660
catcatctca acactgactg atatctggag ccacccgcag ttcgaaaagt gacccatcgc    9720
tagaactagt ggatcttggc tactcaggct ccgacctgga catgacgatt ccaaacttca    9780
gactcggaac ttacgaggag accggacttg ccagattcta aggagacgtg aaggacata    9840 ccgcttttga gaagcgtgtt tgaaaatagt tcttttctg gtttatatcg tttatgaagt    9900
gatgagatga aaagctgaaa tagcgagtat aggaaaattt aatgaaaatt aaattaaata    9960
ttttcttagg ctattagtca ccttcaaaat gccggccgct tctaagaacg ttgtcatgat    10020
cgacaactac gactcgttta cctggaacct gtacgagtac ctgtgtcagg agggagccaa    10080
tgtcgaggtt ttcaggaacg atcagatcac cattccggag attgagcagc tcaagccgga    10140
cgttgtggtg atgggctgca ggaatta                                        10167

<210> SEQ ID NO 7
<211> LENGTH: 8754
<212> TYPE: DNA
<213> ORGANISM: Artificial Sequence
<220> FEATURE:
<223> OTHER INFORMATION: pHSAft-1-IL-2 sequence
<220> FEATURE:
<221> NAME/KEY: gene
<222> LOCATION: (7370)..(7780)
<223> OTHER INFORMATION: Human serum albumin
<220> FEATURE:
<221> NAME/KEY: gene
<222> LOCATION: (7787)..(7810)
<223> OTHER INFORMATION: His tag
<220> FEATURE:
<221> NAME/KEY: gene
<222> LOCATION: (7811)..(7840)
<223> OTHER INFORMATION: Linker
<220> FEATURE:
<221> NAME/KEY: gene
<222> LOCATION: (7841)..(7861)
<223> OTHER INFORMATION: TEV site
<220> FEATURE:
<221> NAME/KEY: gene
<222> LOCATION: (7868)..(8266)
<223> OTHER INFORMATION: Interleukin-2
<220> FEATURE:
<221> NAME/KEY: gene
<222> LOCATION: (8273)..(8296)
<223> OTHER INFORMATION: Strep-tag

<400> SEQUENCE: 7
```

```
gcttatcggg ccgctctagg atcctacttt tttttctccc ttatttagtt cttgagtagc      60
ttggccacct cctgcgcaac agcatcacca acttcctgtg ttgaggagct tccacccaaa     120
tcggcagtca tgatacctgc atccaggacg ttcttgacgg cctgctcgat cgcacggccg     180
gcatccacca agtccagcga cagcttcagc atcatggcgg cagacaaaat tgtggccaat     240
ggattgacct tgcccgggcc caaatctggc gccgagccgt ggcagggctc gtaaagacca     300
aacgccttgt ttgtgtctgg cagagacgcc aacgaggcag aaggcagcag gcccagagac     360
ccaggaatca cactggcctc gtcactgatg atgtcgccaa acatgttgtt ggtgacaatg     420
acaccgttga gtttcgttgg cgacttgacc aaaatcatgg ctgccgagtc gatcagctgg     480
tgctgcaccg tcagctgcgg gaactcgttc ttgatggtct cctcaacagt cttccgccac     540
aaacgcgagg atgcaagcac gttggctttg tccagcgacc acagtgggag cggtgggtcg     600
ctctgcagcg ccaaaaaggc cgccattctc gtgattctct gcacctctgg aacagaatag     660
ctctcagtgt cgctggcaac tccgtcgccg gcatcctcct tgcggtcacc aaagtagatt     720
ccaccaacca actcacgcac aacaacaaag tcagtgccct tgacgatttc tgatttcagt     780
ggagatagct tcagaagagc gtcggaagca aaactgcatg gacgcaggtt cgcgtacaag     840
ttgagctctt ttctgatctt caacagaccc tgctcaggac gcacggagcc ggttccccac     900
ttaggtcctc cgacggctcc aagcaaaacg gcgtcagcct tcttggcggc ttcgagggcc     960
tcgtcggaca atggcacccc ataagcatcg atcgaggcac cgccgatcag gtgcttggaa    1020
aagttgaact taacgccgat gccgacgag acagcctcga aaccttgac ggcctccgca     1080 acaacctcgg ggcccacgtg atcaccaggg agaagcacaa tgttcttact catgattgca    1140
aaatgatgca actattttgc gccggtaccg ggaaaaattg aaaaaccatc cacttactca    1200
ttcctgtctt tttatttcgt attaccaaac cgcttacgta ctcacccact cagatccccc    1260
gggctgcagg aattggatcc gaccagtctc tctcgcacat tatcaattgc tctttagtac    1320
aaagataata tagaaacaat attcgaatta attcgttatg agccatattc aacgggaaac    1380
gtcttgctcg aggccgcgat taaattccaa catggatgct gatttatatg gtataaatg     1440 ggctcgcgat aatgtcgggc aatcaggtgc gacaatctat cgattgtatg ggaagcccga    1500
tgcgccagag ttgtttctga acatggcaa aggtagcgtt gccaatgatg ttacagatga     1560
gatggtcaga ctaaactggc tgacggaatt tatgcctctt ccgaccatca agcattttat    1620
ccgtactcct gatgatgcat ggttactcac cactgcgatc cccgggaaaa cagcattcca    1680
ggtattagaa gaatatcctg attcaggtga aaatattgtt gatgcgctgg cagtgttcct    1740
gcgccggttg cattcgattc ctgtttgtaa ttgtcctttt aacagcgatc gcgtatttcg    1800
tctcgctcag gcgcaatcac gaatgaataa cggtttggtt gatgcgagtg attttgatga    1860
cgagcgtaat ggctggcctg ttgaacaagt ctggaaagaa atgcataagc ttttgccatt    1920
ctcaccggat tcagtcgtca ctcatggtga tttctcactt gataaccttt ttttgacga     1980 ggggaaatta ataggttgta ttgatgttgg acgagtcgga atcgcagacc gataccagga    2040
tcttgccatc ctatggaact gcctcggtga gttttctcct tcattacaga acggcttttt    2100
tcaaaaatat ggtattgata atcctgatat gaataaattg cagtttcatt tgatgctcga    2160
tgagtttttc taatcagaat tggttaattg gttgtaacac tggcagagca ttacgctgac    2220
ttgacgggac ggcggctttg ttgaataaat cgaacttttg ctgagttgaa ggatcagatc    2280
acgcatcttc ccgacaacgc agaccgttcc gtggcaaagc aaaagttcaa aatcaccaac    2340
tggtccacct acaacaaagc tctcatcaac cgtggctccc tcactttctg ctggatgat     2400
```

```
ggggcgattc aggcctggta tgagtcagca acaccttctt cacgaggcag acctcagcgc    2460 cccccccct gcagtcgaca ggccaacgtg gttgtggcgg agtcggtggt gtttagagag    2520
gaattagagc aagtagaagt atagaaggaa taagccaagt agagacaagt ttaatatatg    2580
tagattaata aaggtgagga attagatggg gaggaagcgg caggaagcgg tgtagggatg    2640
cggcgaggaa agcagaggca gctggtttca ggacgcggtc tgaggcctgg ggtggcgggg    2700
tggcggggtg gcggggtggc ggggtggcgg ggtggcgggg tggcggggtg gcggggtggc    2760
ggggtggcgg ggtggcgggg tggcggggtg gcggggtggc ggggtggcgg ggtggcgggg    2820
tggcggggtg gcggggtggc ggggtggcgg ggtggcgggg tggcggggtg gcgatcaagc    2880
ttatcgatac cgtcgacctc gaggggggggc ccggtaccca gcttttgttc cctttagtga    2940
gggttaattg cgcgcttggc gtaatcatgg tcatagctgt ttcctgtgtg aaattgttat    3000
ccgctcacaa ttccacacaa catacgagcc ggaagcataa agtgtaaagc ctggggtgcc    3060
taatgagtga gctaactcac attaattgcg ttgcgctcac tgcccgcttt ccagtcggga    3120
aacctgtcgt gccagctgca ttaatgaatc ggccaacgcg cggggagagg cggtttgcgt    3180
attgggcgct cttccgcttc ctcgctcact gactcgctgc gctcggtcgt tcggctgcgg    3240
cgagcggtat cagctcactc aaaggcggta atacggttat ccacagaatc aggggataac    3300
gcaggaaaga acatgtgagc aaaaggccag caaaaggcca ggaaccgtaa aaaggccgcg    3360
ttgctggcgt ttttccatag gctccgcccc cctgacgagc atcacaaaaa tcgacgctca    3420
agtcagaggt ggcgaaaccc gacaggacta taaagatacc aggcgtttcc ccctggaagc    3480
tccctcgtgc gctctcctgt tccgaccctg ccgcttaccg gatacctgtc cgcctttctc    3540
ccttcgggaa gcgtggcgct ttctcatagc tcacgctgta ggtatctcag ttcggtgtag    3600
gtcgttcgct ccaagctggg ctgtgtgcac gaaccccccg ttcagcccga ccgctgcgcc    3660
ttatccggta actatcgtct tgagtccaac ccggtaagac acgacttatc gccactggca    3720
gcagccactg gtaacaggat tagcagagcg aggtatgtag gcggtgctac agagttcttg    3780
aagtggtggc ctaactacgg ctacactaga aggacagtat ttggtatctg cgctctgctg    3840
aagccagtta ccttcggaaa aagagttggt agctcttgat ccggcaaaca aaccaccgct    3900
ggtagcggtg ttttttttgt ttgcaagcag cagattacgc gcagaaaaaa aggatctcaa    3960
gaagatcctt tgatcttttc tacggggtct gacgctcagt ggaacgaaaa ctcacgttaa    4020
gggattttgg tcatgagatt atcaaaaagg atcttcacct agatcctttt aaattaaaaa    4080
tgaagtttta aatcaatcta agtatatat gagtaaactt ggtctgacag ttaccaatgc    4140
ttaatcagtg aggcacctat ctcagcgatc tgtctatttc gttcatccat agttgcctga    4200
ctccccgtcg tgtagataac tacgatacgg gagggcttac catctggccc cagtgctgca    4260
atgataccgc gagacccacg ctcaccggct ccagatttat cagcaataaa ccagccagcc    4320
ggaagggccg agcgcagaag tggtcctgca actttatccg cctccatcca gtctattaat    4380
tgttgccggg aagctagagt aagtagttcg ccagttaata gtttgcgcaa cgttgttgcc    4440
attgctacag gcatcgtggt gtcacgctcg tcgtttggta tggcttcatt cagctccggt    4500
tcccaacgat caaggcgagt tacatgatcc cccatgttgt gcaaaaaagc ggttagctcc    4560
ttcggtcctc cgatcgttgt cagaagtaag ttggccgcag tgttatcact catggttatg    4620
gcagcactgc ataattctct tactgtcatg ccatccgtaa gatgcttttc tgtgactggt    4680
gagtactcaa ccaagtcatt ctgagaatag tgtatgcggc gaccgagttg ctcttgcccg    4740
```

```
gcgtcaatac gggataatac cgcgccacat agcagaactt taaaagtgct catcattgga   4800
aaacgttctt cggggcgaaa actctcaagg atcttaccgc tgttgagatc cagttcgatg   4860
taacccactc gtgcacccaa ctgatcttca gcatctttta ctttcaccag cgtttctggg   4920
tgagcaaaaa caggaaggca aaatgccgca aaaagggaa taagggcgac acggaaatgt    4980
tgaatactca tactcttcct ttttcaatat tattgaagca tttatcaggg ttattgtctc   5040
atgagcggat acatatttga atgtatttag aaaataaac aaatagggt tccgcgcaca     5100 tttcccccgaa aagtgccacc taaattgtaa gcgttaatat tttgttaaaa ttcgcgttaa  5160
atttttgtta aatcagctca tttttaacc aataggccga atcggcaaa atcccttata     5220 aatcaaaaga atagaccgag atagggttga gtgttgttcc agtttggaac aagagtccac   5280
tattaaagaa cgtggactcc aacgtcaaag ggcgaaaaac cgtctatcag ggcgatggcc   5340
cactacgtga accatcaccc taatcaagtt ttttggggtc gaggtgccgt aaagcactaa   5400
atcggaaccc taaagggagc ccccgattta gagcttgacg gggaaagccg cgaacgtgg    5460 cgagaaagga agggaagaaa gcgaaaggag cgggcgctag ggcgctggca agtgtagcgg   5520
tcacgctgcg cgtaaccacc acccgccg cgcttaatgc gccgctacag ggcgcgtccc     5580
attcgccatt caggctgcgc aactgttggg aagggcgatc ggtgcgggcc tcttcgctat   5640
tacgccagct ggcgaaaggg ggatgtgctg caaggcgatt aagttgggta acgccagggt   5700
tttcccagtc acgacgttgt aaaacgacg ccagtgagcg cgcgtaatac gactcactat    5760
agggcgaatt ggagctccac cgcggtggcg gccgtcgatc gacgcgaaga acgatctcct   5820
cgagctgttc gcggatcagc ttgtagccct gcagtggaac caggccgacg gcccgctcct   5880
tgcggaccac ggtggctggc gcgcccaatt tgtgaaccag gtcgtttagg acctcctgcg   5940
caaagtccag tgttaggaga atgtcctcct gggaccaatt cagcatgttc tcgagcagcc   6000
atctgtcttt ggagtaaaaa cgtaatttct gctcctcgtt actgtaccgg aaaagataat   6060
ttgcctcgcc gcccataata agaaggttct ttttctggtg gcctttgagc agcgggacg    6120 tttggacagc gtcgatgagg ccccttgaggc gctcgtagta cttggtcgcg tcgttgtagc  6180
cggccgcggt gacgataccc acataaaggt ctttggccat tagcttgatg aggtggggta   6240
agatgggcga ctcggcatcg aaattttttgc cgtcgtcgta cagtgtgatg tcaccatcga   6300
atgttatgag ctgcagcttg cgatctcgga tggttttgga atggaagaac cgcgacatct   6360
ccaacagctg ggccgtgttg aggatgagcc ggacgtcgtt gaacgagggc gccacaagcc   6420
ggcgtttgct gatggcgcgg cgctcgtcct cgatgtagaa ggccttttcc agaggcagtc   6480
tggtgaaaaa gttgccaacg ctcggaacca gctgcacgag ccgagacaat tcgggggtgc   6540
cggctttggt catttcaatg ttgtcgtcga tgaggagttc gaggtcgtgg aagatttctg   6600
cgtaacggcg ttttgcctca gagttcacca tgagatcgtc cacggcggag atgccgttgc   6660
tcttcaccgc gtacaggacg aacgcgtgg ccaacaggcc ctttatccac tctatgaggc    6720
cgtctcgacg gtgttccttg agtgcatact ccactctgta gcgactagtc atccggaggc   6780
tgggctttct gcgctgggtg tactaattaa ttggtgccgc acctgtacgg ggtaccttgc   6840
atccttgcac cgcaactaaa ataaacccac tcgctttagc cttcgcgtaa aactcgtgaa   6900
tctggcaact gagggggttc tgcagccgca accaaacttt atcgctttga ggacgcagct   6960
ggatggtgtc atgtgaggct ctgttctctg gcgtagccta caacgtgact ttgcctaagc   7020 ggacggcccct acccttagct gcctgcgcct gctaccagaa aatcactaga acagcagagg   7080
gccgatgtgg taattggtgc ggtgtcggcc agtctgtttc tccacagtgc aaatgcgggt   7140
```

```
gaaccggcca gaaagcaaat ttcttatgct accgtgcagt gactccgaca tccccagttt    7200
ttgccctact tgatcacaga tggggtcagc actgtcgcta agtgcaccca gtcgtcccca    7260
cacgcgcaat ctataaatac tgccgccagt gcacggtggt gacatcaatc taaagtacaa    7320
aaacaaaagc ttgaattcgg cacgaggtca accccacgcc tttggcacaa tgaagtgggt    7380
aacctttatt tcccttcttt ttctctttag ctcggcttat tccaggggtg tgtttcgtcg    7440
agatgcacac aagagtgagg ttgctcatcg gtttaaagat tgggagaag aaaatttcaa     7500 agccttggtg ttgattgcct ttgctcagta tcttcagcag tgtccatttg aagatcatgt    7560
aaaattagtg aatgaagtaa ctgaatttgc aaaaacatgt gttgctgatg agtcagctga    7620
aaattgtgac aaatcacttc atacccttt tggagacaaa ttatgcacag ttgcaactct     7680
tcgtgaaacc tatggtgaaa tggctgactg ctgtgcaaaa caagaacctg agagaaatga    7740
atgcttcttg caacacaaag atgacaatcc aaatctcccc gttaaccatc accatcacca    7800
tcaccatcac ggtggcggtg gctcgggtgg cgtggatcc gaaaacctgt attttcaggg     7860
cgctagcatg cctacttcaa gttctacaaa gaaaacacag ctacaactgg aacatttact    7920
gctggattta cagatgattt tgaatggaat taataattac aagaatccca aactcaccag    7980
gatgctcaca tttaagtttt acatgcccaa gaaggccaca gaattgaaac atcttcagtg    8040
tctagaagaa gaactcaaac ctctggagga agtgctaaat ttagctcaaa gcaaaaactt    8100
tcacttaaga cccagggact taatcagcaa tatcaacgta atagttctgg aactaaaggg    8160
atctgaaaca acattcatgt gtgaatatgc tgatgagaca gcaaccattg tagaatttct    8220
gaacagatgg attacctttt ctcagagcat catctcaaca ctgactgata tctggagcca    8280
cccgcagttc gaaaagtgac ccatcgctag aactagtgga tcttggctac tcaggctccg    8340
acctggacat gacgattcca aacttcagac tcggaactta cgaggagacc ggacttgcca    8400
gattctaagg agacgtggaa ggacataccg cttttgagaa gcgtgtttga aaatagttct    8460
ttttctggtt tatatcgttt atgaagtgat gagatgaaaa gctgaaatag cgagtatagg    8520
aaaatttaat gaaattaaa ttaaatattt tcttaggcta ttagtcacct tcaaaatgcc     8580
ggccgcttct aagaacgttg tcatgatcga caactacgac tcgtttacct ggaacctgta    8640
cgagtacctg tgtcaggagg gagccaatgt cgaggttttc aggaacgatc agatcaccat    8700
tccggagatt gagcagctca agccggacgt tgtggtgatg ggctgcagga atta          8754

<210> SEQ ID NO 8
<211> LENGTH: 54
<212> TYPE: DNA
<213> ORGANISM: Artificial Sequence
<220> FEATURE:
<223> OTHER INFORMATION: TAG-d1 primer

<400> SEQUENCE: 8
tttgttaacc acccgcagtt ggaaaagtga cccgggaagc ttggcactgg ccgt          54

<210> SEQ ID NO 9
<211> LENGTH: 45
<212> TYPE: DNA
<213> ORGANISM: Artificial Sequence
<220> FEATURE:
<223> OTHER INFORMATION: TAG-d2 primer

<400> SEQUENCE: 9
aaagctagcg gccgcgatat ctggagccac ccgcagttcg aaaag                    45
```

```
<210> SEQ ID NO 10
<211> LENGTH: 51
<212> TYPE: DNA
<213> ORGANISM: Artificial Sequence
<220> FEATURE:
<223> OTHER INFORMATION: TAG-u2 primer

<400> SEQUENCE: 10
gtggctagcg ccctgaaaat acaggttttc ggatccaccg ccacccgagc c         51

<210> SEQ ID NO 11
<211> LENGTH: 21
<212> TYPE: DNA
<213> ORGANISM: Artificial Sequence
<220> FEATURE:
<223> OTHER INFORMATION: HSA-F primer

<400> SEQUENCE: 11
ctcaagcttg aattcggcac g                                           21

<210> SEQ ID NO 12
<211> LENGTH: 34
<212> TYPE: DNA
<213> ORGANISM: Artificial Sequence
<220> FEATURE:
<223> OTHER INFORMATION: HSA-u1 primer

<400> SEQUENCE: 12
tttgttaacg ggggagattt ggattgtcat cttt                             34

<210> SEQ ID NO 13
<211> LENGTH: 36
<212> TYPE: DNA
<213> ORGANISM: Artificial Sequence
<220> FEATURE:
<223> OTHER INFORMATION: HSA-u5 primer

<400> SEQUENCE: 13
tttgttaact aagcctaagg cagcttgact tgcagc                           36

<210> SEQ ID NO 14
<211> LENGTH: 29
<212> TYPE: DNA
<213> ORGANISM: Artificial Sequence
<220> FEATURE:
<223> OTHER INFORMATION: IL-2-F primer

<400> SEQUENCE: 14
ctagctagca tgcctacttc aagttctac                                   29

<210> SEQ ID NO 15
<211> LENGTH: 47
<212> TYPE: DNA
<213> ORGANISM: Artificial Sequence
<220> FEATURE:
<223> OTHER INFORMATION: IL-2-R (w/His-Tag) primer

<400> SEQUENCE: 15
gcttgatatc tcagtggtgg tggtggtggt gagtcagtgt tgagatg               47
```